(12) United States Patent
Hendricks et al.

(10) Patent No.: US 6,387,907 B1
(45) Date of Patent: May 14, 2002

(54) USE OF SEROTONIN AGONISTS TO ALLEVIATE DISORDERED BREATHING EPISODES IN A MAMMAL

(75) Inventors: Joan C. Hendricks, Fort Washington; Leszek Kubin, Havertown; Allan I. Pack, Glen Mills; Sigrid C. Veasey, Philadelphia, all of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/439,799

(22) Filed: Nov. 12, 1999

Related U.S. Application Data

(63) Continuation of application No. PCT/US98/09976, filed on May 15, 1998
(60) Provisional application No. 60/046,654, filed on May 16, 1997.

(51) Int. Cl.$^7$ ...................... A61K 31/495; A61K 31/40; A61K 31/135
(52) U.S. Cl. ................... 514/254.06; 514/419; 514/649
(58) Field of Search ........................... 514/649, 254.06, 514/419

(56) References Cited

U.S. PATENT DOCUMENTS 4,329,356 A * 5/1982 Holland

OTHER PUBLICATIONS

Curzon et al., 1990, TIPS 11:181.
Devaud et al., 1992, J. Neurochem. 59:1459–1466.
Galvin et al., 1989, Radiology 171:775–778.
Hanzel et al., 1991, Chest 100:416–421.
Hendricks et al., 1987, J. Appl. Physiol. 63:1344–1350.
Hendricks et al., 1991, Am. Rev. Respir. Dis. 144:1112–1120.
Hendricks et al., 1993, Am. Rev. Respir. Dis. 148:185–194.
Itoh et al., 1995, J. Pharmacy Pharmacol. 47:833–836.
Koss, 1991, Eur. J. Pharmacol. 194:161–166.
Kubin et al., 1992, Neurosci. Lett. 139:243–248.
Kubin et al., 1993, Brain Res. 611:300–312.
Magalang et al., 1996, Sleep Res. 25:16.
Manaker et al., 1993, J. Comp. Neurol. 334:466–476.
Mendelson et al., 1991, J. Clin. Psychopharmacol. 11:71–72.
Mezzanote et al., 1989, J. Clin. Invest. 89:1571–1579.
Remmers et al., 1978, J. Appl. Physiol. 44:931–938.
Ribeiro–do–Valle et al., 1991, Brain Res. 550:197–204.
Salazar–Grueso et al., 1988, Ann. Neurol. 23:394–401.
Schwab et al., 1993, Am. Rev. Respir. Dis. 148:1385–1400.
Schwab et al., 1993, J. Appl. Physiol. 74:1504–1514.
Soja et al., 1987, Exp. Neurol. 96:178–93.
Strohl et al., 1987, Chest 92:918–920.

* cited by examiner

Primary Examiner—William R. A. Jarvis
(74) Attorney, Agent, or Firm—Morgan, Lewis & Bockius, LLP

(57) ABSTRACT

The invention includes compositions for alleviating or preventing a disordered breathing episode. The composition of the invention comprises a serotonin re-uptake inhibitor, a TRH agonist and an agent selected from the group consisting of a serotonin precursor and a serotonin agonist.

12 Claims, 12 Drawing Sheets

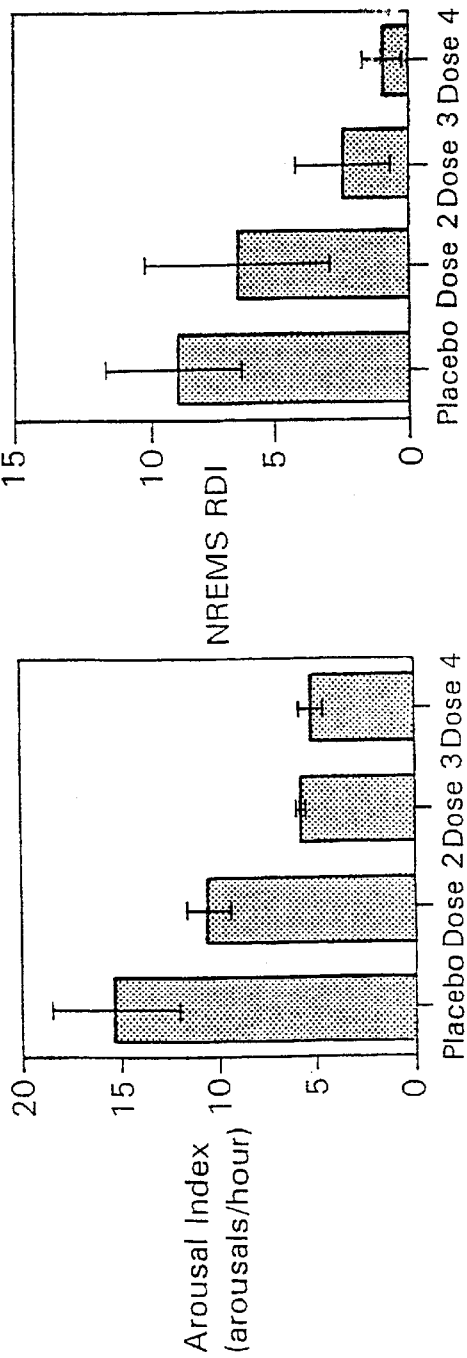
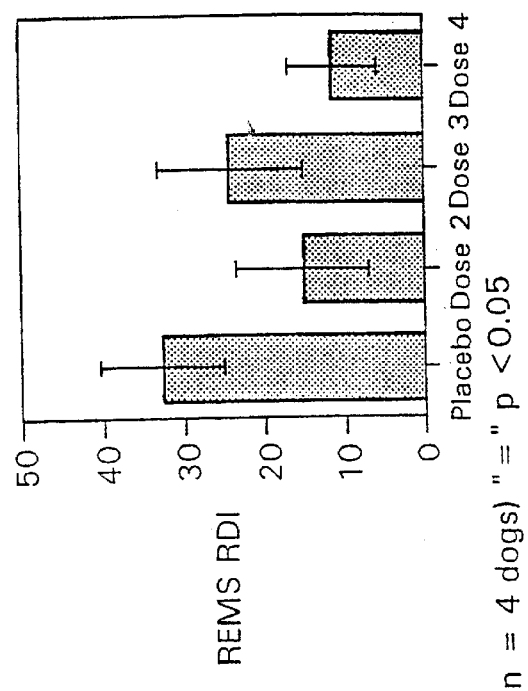
Fig. 1A
Fig. 1B
Fig. 1C
Group data (n = 4 dogs) "=" $p < 0.05$

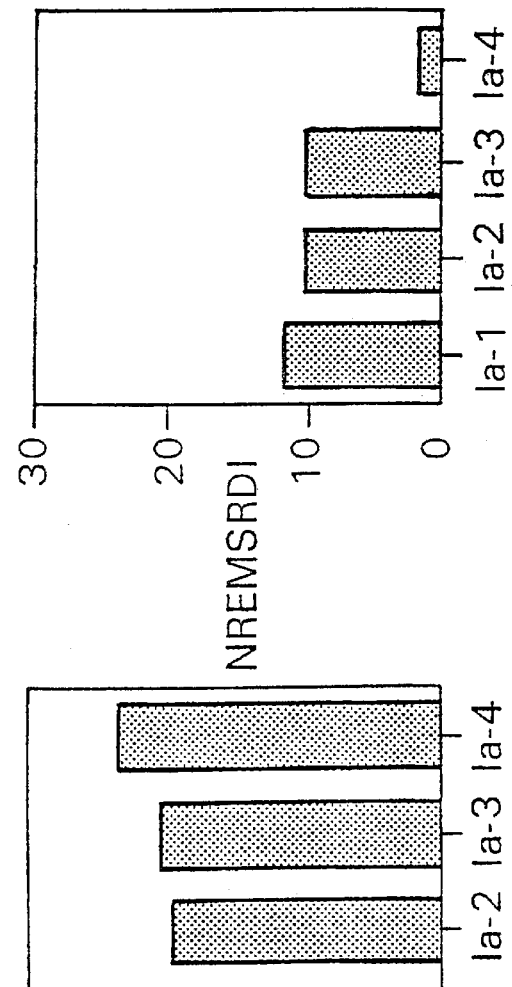
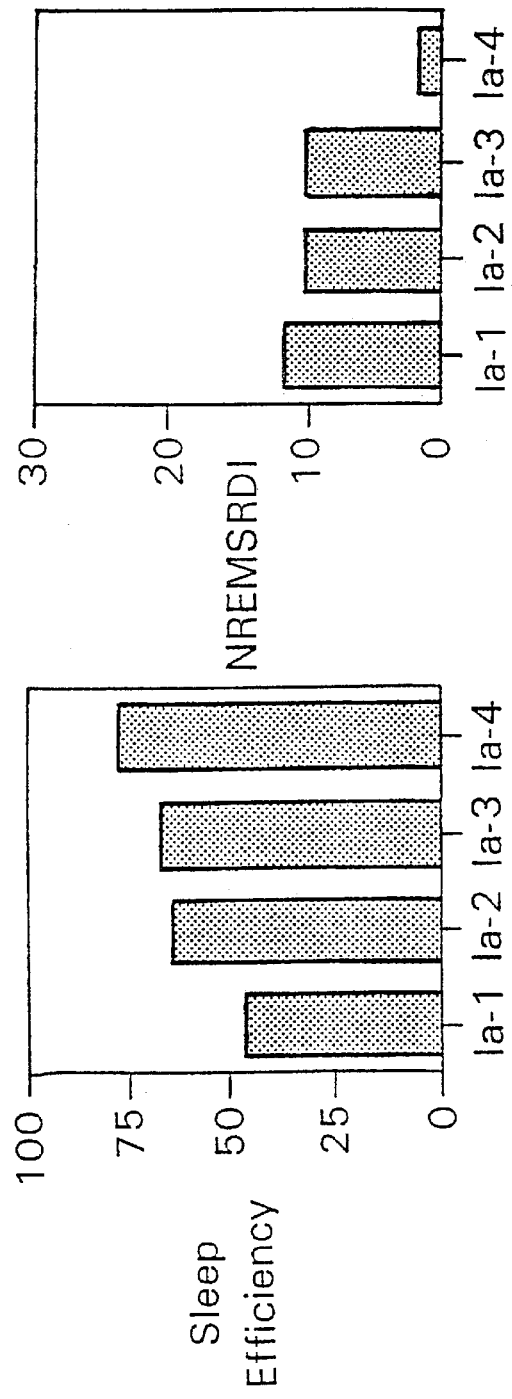
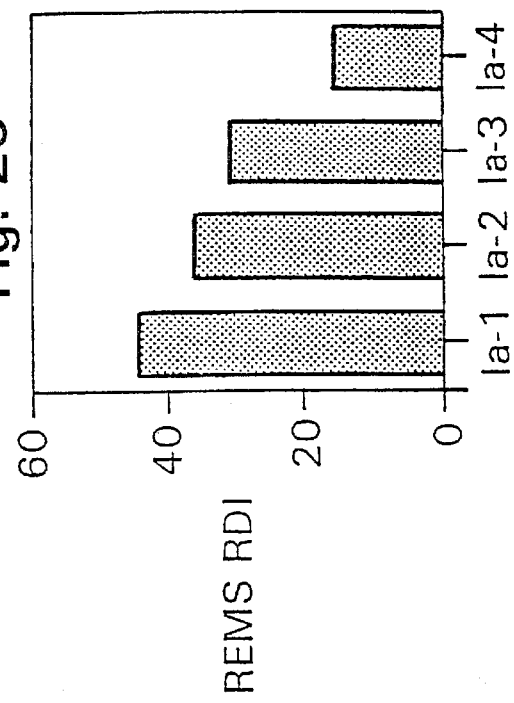
Fig. 2A
Fig. 2B
Fig. 2C

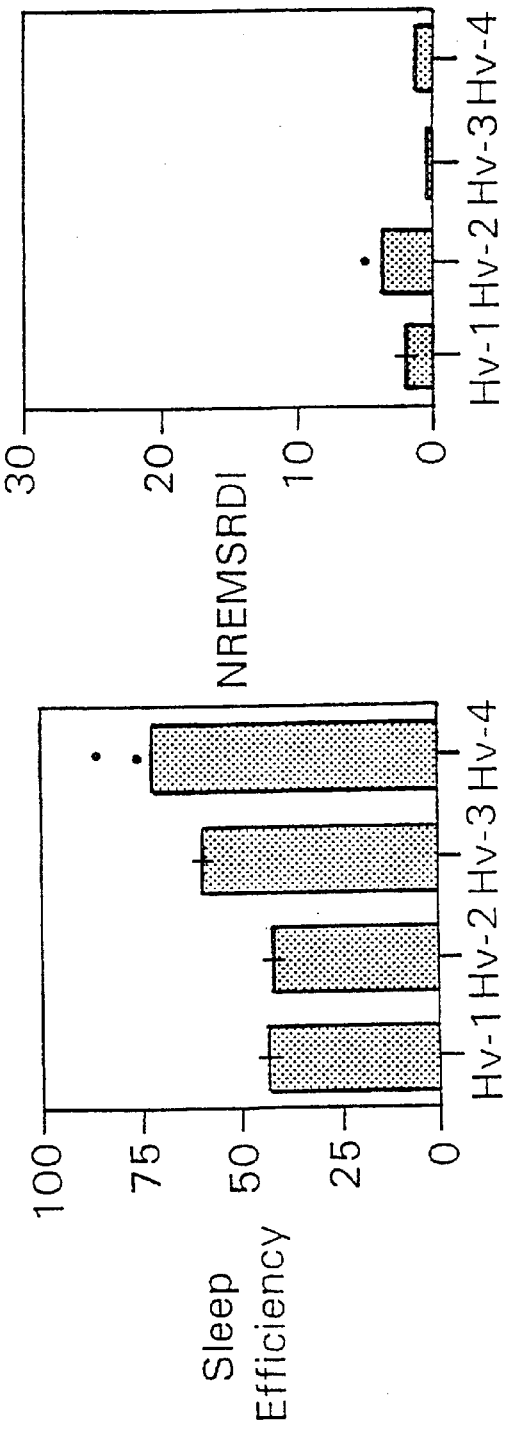
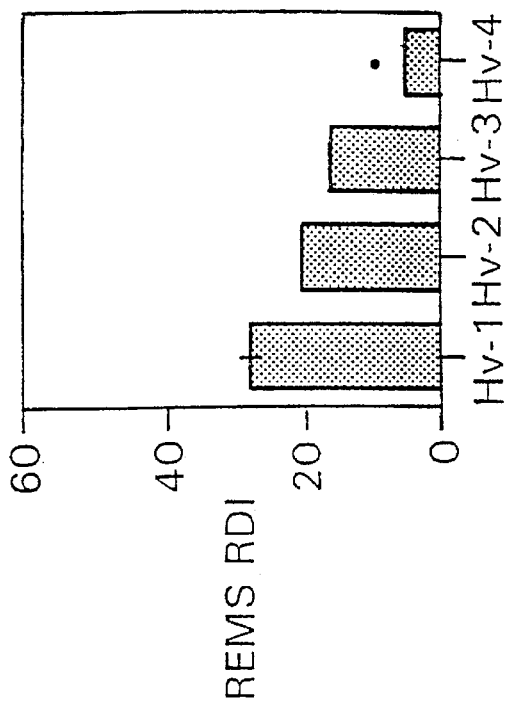
Fig. 2D
Fig. 2E
Fig. 2F

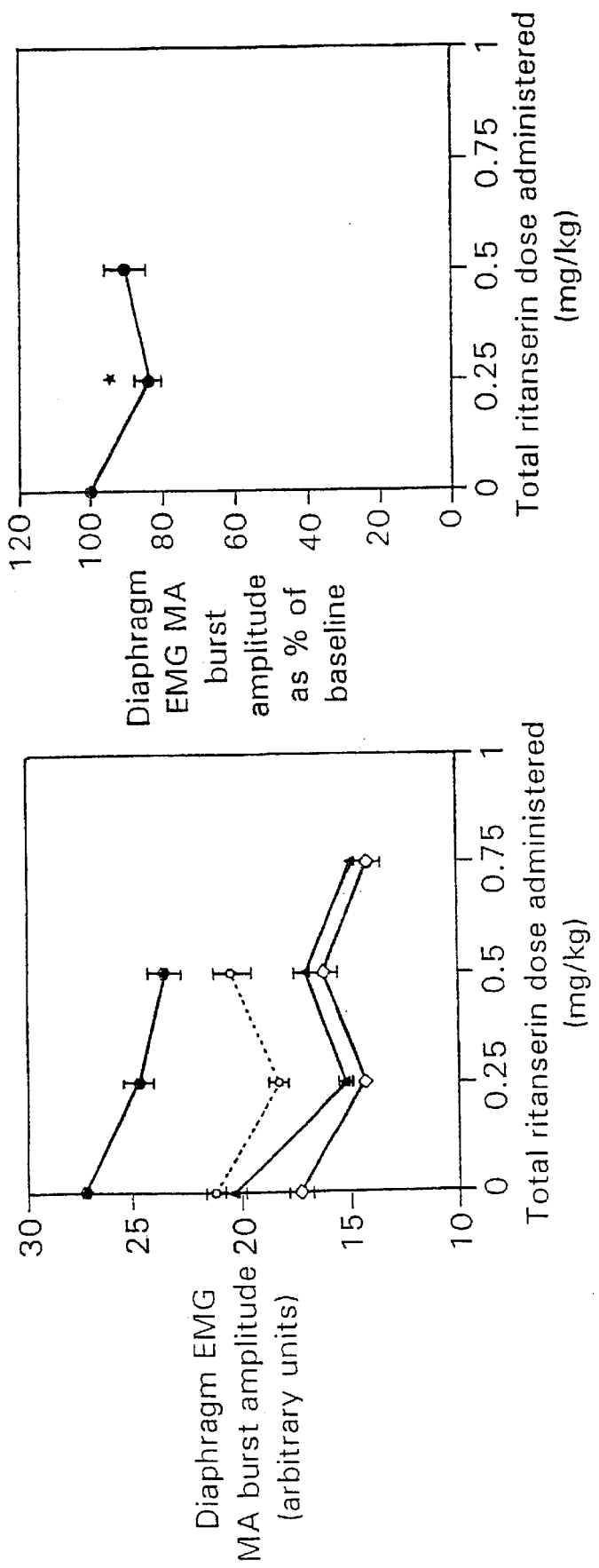

USE OF SEROTONIN AGONISTS TO ALLEVIATE DISORDERED BREATHING EPISODES IN A MAMMAL

This application is a continuation of PCT/US 98/09976, filed May 15, 1998, which claims benefit of provisional application No. 60/046,654, filed May 16, 1997.

FIELD OF THE INVENTION

The invention relates to treatment of disordered breathing episodes.

BACKGROUND OF THE INVENTION

Sleep disturbance is a primary reason why many people do not feel rested after a night's sleep. Sleep disturbance diminishes the productivity and quality of life of individuals who experience it. One class of disorders which disturb sleep is obstructive sleep-disordered breathing, in which loss of upper airway patency prevents or interrupts restful sleep.

Upper airway patency in mammals is modulated by upper airway anatomy and dilatory muscle activity. Reduced activity of these muscles can lead to a narrowing or obstruction of the upper airway, with the result that normal breathing is interfered with or interrupted (Remmers et al., 1978, J. Appl. Physiol. 44:931–938; Strohl et al., 1987, Chest 92:918–920). An episode of interference with or interruption of normal breathing caused by collapse of the upper airway is designated a disordered breathing episode. These are also commonly referred to as apneas, hypopneas, and respiratory effort-related arousals.

There is evidence that certain individuals are anatomically predisposed to disordered breathing episodes, these individuals having upper airway passages which are narrower than those in individuals who do not regularly experienced disordered breathing episodes. In sleep, activity of upper airway dilatory muscles is reduced, and this may cause sleep-disordered breathing episodes.

Obstructive sleep-disordered breathing is prevalent in humans, is associated with significant morbidity and mortality, and is a condition for which there are no well-tolerated, universally-effective pharmacotherapies. It is estimated that twenty million persons in the United States are afflicted with sleep apnea, a less precise term for obstructive sleep-&ordered breathing. Sleep apnea is a condition associated with disordered breathing episodes which disturb or interrupt sleep. Thus, the need for an effective treatment or preventative for episodes of disordered breathing is severe.

The physiological or biochemical mechanisms which underlie loss of upper airway patency are not well understood. It is known that apneas tend to be longer and more severe during rapid eye movement (REM) sleep than during other periods of sleep (Findley et al., 1985, Chest 87:432436). Unlike the postural muscle atonia of REM sleep, upper airway muscle atonia is not mediated primarily through a glycinergic post-synaptic inhibition of the relevant motoneurons (Morales et al., 1981, Brain Res. 225:279–295; Soja et al., 1987, Exp. Neurol. 96:178–93; Kubin et al., 1993, Brain Res. 611:300–312). Thus, withdrawal of excitory stimuli from hypoglossal motoneurons during REM sleep likely accounts for much of the suppression of motor activity of upper airway musculature (Kubin et al., 1993, Brain Res. 611:300–312). Microinjection of serotonin into brainstem motor nuclei in vivo results in increased activity of muscles innervated by trigeminal neurons and increased activity of hypoglossal motoneurons (Ribeiro-do-Valle et al., 1991, Brain Res. 550:197–204; Kubin et al., 1992, Neurosci. Lett. 139:243–248). Microinjection of a thyrotropin-releasing hormone (TRH) analog into the hypoglossal nucleus produces a powerful respiratory-related excitation of hypoglossal motoneurons (Magalang et al., 1996, Sleep Res. 25:16). The primary source of both serotonin and TRH for hypoglossal motoneurons is serotonergic neurons within the caudal medullary nuclei raphe obsurus and raphe pallidus, which are two of the raphe nuclei of the mammalian brainstem (Manaker et al., 1993, J. Comp. Neurol. 334:466–476; Hokfelt et al;, 1980, In: *Neural Peptides and Neural Communication*, Trabucchi, Ed., Raven press, New York, pp. 1–23). The firing rate of these serotonergic neurons is reduced during non-REM sleep. Furthermore, many of these serotonergic neurons cease firing during REM sleep (Heym et al., 1982, Brain Res. 251:259–276).

An animal model of sleep-disordered breathing in humans has been described, namely the English bulldog (Hendricks et al., 1987, J. Appl. Physiol. 63:1344–1350). English bulldogs have significantly narrowed upper airways, daytime hypersomnolence, shortened sleep latencies, and frequent sleep-disordered breathing episodes that are most pronounced during REM sleep (Hendricks et al., 1987, J. Appl. Physiol. 63:1344–1350). Recent studies using this animal model have demonstrated that sleep-disordered breathing episodes occur most frequently in association with the phasic reductions in upper airway dilator muscle activity that occur during REM sleep (Hendricks et al., 1991, Am. Rev. Respir. Dis. 144:1112–1120). Furthermore, normal respiration during waking and sleep in this animal model is associated with augmented upper airway motor activity, just as it is in persons afflicted with obstructive sleep apnea (Hendricks et al., 1993, Am. Rev. Respir. Dis. 148:185–194; Mezzanote et al., 1989, J. Clin. Invest. 89:1571–1579).

Sleep-disordered breathing episodes cause snoring, hypersomnolence, and frequent sleep interruption. Persons who experience such episodes may be less alert than they would be in the absence of such episodes and may not be able to experience restful sleep. Thus, both the productivity and the quality of life of these persons would be greatly increased if their sleep-disordered breathing episodes could be modulated or eliminated. Compositions which have been used to treat sleep apnea have each included one of the following ingredients: the antidepressant protriptyline, the serotonin re-uptake inhibitors fluoxetine and trazadone, the anxiolytic buspirone, and L-tryptophan (Hanzel et al., 1991, Chest 100:416–421; Salazar-Grueso et al., 1988, Ann. Neurol. 23:394–401; Mendelson et al., 1991, J. Clin. Psychopharmacol. 11:71–72; Schmidt, 1983, Bull Eur. Physiopath. Resp. 19:625–629). Administration of these compounds treated sleep apnea in patients with mixed results. The present invention provides improved, and thus more effective, compositions and methods for modulating or eliminating disordered breathing episodes, including episodes of sleep-disordered breathing such as obstructive sleep apnea.

SUMMARY OF THE INVENTION

The invention relates to a composition for alleviating or preventing a disordered breathing episode in a mammal. The composition comprises a serotonin re-uptake inhibitor and an agent selected from the group consisting of a serotonin precursor and a serotonin agonist.

In one embodiment of the composition of the invention, the serotonin re-uptake inhibitor is selected from the group consisting of trazadone, fluoxetine, and nefazodone.

In another embodiment of the composition of the invention, the serotonin precursor is selected from the group consisting of L-tryptophan and L-5-hydroxytryptophan.

In yet another embodiment of the composition of the invention, the serotonin re-uptake inhibitor comprises trazadone, the serotonin precursor comprises L-tryptophan, and the ratio, by weight, of L-tryptophan to trazodone is between about 13.3 to 1 and about 13.5 to 1.

In still another embodiment of the composition of the invention, the serotonin agonist is selected from the group consisting of serotonin, 5-CT, and DOI.

In one aspect, the composition of the invention comprises both the serotonin precursor and the serotonin agonist. In another aspect, the composition further comprises a TRH agonist, such as one selected from the group consisting of TRH, montirelin, and CG-3703.

The invention also relates to a kit for alleviating or preventing a disordered breathing episode in a mammal. The kit comprises a serotonin re-uptake inhibitor and an agent selected from the group consisting of a serotonin precursor and a serotonin agonist.

In one embodiment of the kit of the invention, the agent is selected from the group consisting of L-tryptophan, L-5-hydroxytryptophan, serotonin, 5-CT, and DOI and is in a unit dosage form.

In another embodiment of the kit of the invention, the serotonin re-uptake inhibitor is selected from the group consisting of trazadone, fluoxetine, and nefazodone and is in a unit dosage form.

In yet another embodiment of the kit of the invention, the unit dosage form of the agent is an oral unit dosage form and wherein the unit dosage form of the serotonin re-uptake inhibitor is an injectable solution.

In still another embodiment of the kit of the invention, the kit further comprises an instructional material describing administration of the serotonin re-uptake inhibitor and the agent for the purpose of alleviating or preventing a disordered breathing episode in a mammal.

The invention further relates to a method of alleviating a disordered breathing episode in a mammal. This method comprises administering a serotonin re-uptake inhibitor to the mammal and administering an agent to the mammal. The disordered breathing episode is thereby alleviated. The serotonin re-uptake inhibitor is administered in an amount effective to enhance or extend the hypoglossal motoneuron-stimulating effect of endogenous serotonin of the mammal. The agent is selected from the group consisting of a serotonin precursor and a serotonin agonist, and is administered in an amount effective to prevent tachyphylaxis associated with administration to the mammal of the serotonin re-uptake inhibitor.

In one embodiment of this method, the mammal is afflicted with a condition associated with a disordered breathing episode, such as one selected from the group consisting of hypersomnolence, snoring, hypopneas, apneas, obstructive sleep apnea, sleep hypopnea syndrome, upper airway resistance syndrome, and severe snoring conditions associated with arousal from sleep. Preferably the mammal is a human.

In another embodiment of this method, the serotonin re-uptake inhibitor is selected from the group consisting of trazadone, fluoxetine, and nefazodone.

In yet another embodiment of this method, the serotonin precursor is selected from the group consisting of L-tryptophan and L-5-hydroxytryptophan, In still another embodiment of this method, the serotonin agonist is selected from the group consisting of serotonin, 5-CT, and DOI.

In another embodiment of this method, both the serotonin precursor and the serotonin agonist are administered to the mammal.

In one aspect, this method further comprises administering a TRH agonist to the mammal. The TRH agonist may, for example, be one selected from the group consisting of TRH, montirelin, and CG-3703.

The invention still further relates to a method of preventing a disordered breathing episode in a mammal imminently anticipated to experience a disordered breathing episode. This method comprises administering a serotonin re-uptake inhibitor to the mammal and administering an agent to the mammal. The disordered breathing episode is thereby alleviated. The serotonin re-uptake inhibitor is administered in an amount effective to enhance or extend the hypoglossal motoneuron-stimulating effect of endogenous serotonin of the mammal. The agent is selected from the group consisting of a serotonin precursor and a serotonin agonist and is administered in an amount effective to prevent tachyphylaxis associated with administration to the mammal of the serotonin re-uptake inhibitor.

In one embodiment of this method, the mammal is afflicted with a condition associated with a disordered breathing episode, such as one selected from the group consisting of hypersomnolence, snoring, hypopneas, apneas, obstructive sleep apnea, sleep hypopnea syndrome, upper airway resistance syndrome, and severe snoring conditions associated with arousal from sleep. Preferably, the mammal is a human.

In another embodiment of this method, the serotonin re-uptake inhibitor is selected from the group consisting of trazadone, fluoxetine, and nefazodone.

In yet another embodiment of this method, the serotonin precursor is selected from the group consisting of L-tryptophan and L-5-hydroxytryptophan.

In still another embodiment of this method, the serotonin agonist is selected from the group consisting of serotonin, 5-CT, and DOI.

In another embodiment of this method, both the serotonin precursor and the serotonin agonist are administered to the mammal.

In aspect, this method further comprises administering a TRH agonist to the mammal, such as one selected from the group consisting of TRH, montirelin, and CG-3703.

BRIEF DESCRIPTION OF THE DRAWINGS

FIG. 1, comprising FIGS. 1A, 1B, and 1C, is a series of histograms showing the effects of trazodone/L-tryptophan on Arousal index, NREMS RDI, and REM RDI in English bulldogs. Group data for four dogs are shown.

FIG. 2, comprising FIGS. 2A, 2B, 2C, 2D, 2E, and 2F, is a series of histograms showing the effects of trazodone/L-tryptophan on Sleep Efficiency, NREMS RDI, and REMS RDI in English bulldogs. Individual data for bulldogs EBD-Ja and EBD-Hu are shown. Data are analyzed with individual repeated measures ANOVA, and asterisks denote significant changes from baseline.

FIG. 3, comprising FIG. 3A depicts geniohyiod (GH) respiratory burst amplitudes in individual bulldogs following administration of one of three doses of ritanserin. FIG. 3B presents the mean data presented individually in FIG. 3A, expressed as a percentage of baseline motor activity. FIG. 3C depicts sternohyoid (SH) burst amplitudes in individual bulldogs following administration of one of three doses of ritanserin. FIG. 3D presents the mean data presented individually in FIG. 3C, expressed as a percentage of baseline activity. FIG. 3E depicts SH burst amplitudes in individual bulldogs following administration of one of three of methysergide. FIG. 3F presents the mean data presented individually in FIG. 3E, expressed as a percentage of baseline activity. Asterisks mark significant ($p<0.0.5$) reductions in dilator muscle activity from baseline. Standard error bars are presented for all data groups.

FIG. 4, comprising FIGS. 4A, 4B, 4C, and 4D, is a series of graphs depicting the effect of administering a serotonin antagonists on respiratory burst amplitudes. FIG. 4A depicts diaphragm (DIA) activity at baseline and following administration of one of three does of ritanserin. FIG. 4B presents the mean data presented individually in FIG. 4A, expressed as a percentage of baseline activity.

FIG. 4C depicts diaphragm (DIA) activity at baseline and following administration of one of two does of methyergide. FIG. 4D presents the mean data presented individually in FIG. 4C, expressed as a percentage of baseline activity.

FIG. 5, comprising FIG. 5A indicates percent suppression of diaphragm (DIA) activity (solid bars) and percent suppression of geniohyiod activity (speckled bars) in individual dogs following administration of 0.25 milligrams per kilogram of body weight of ritanserin. As a group, the suppression in upper airway motor activity was greater than that of the diaphragm ($p<0.05$). FIG. 5B indicates percent suppression of DIA activity (solid bars) and percent suppression of sternohyoid activity (speckled bars) for individual dogs followed administration of 0.50 milligrams per kilogram of body weight of methysergide.

FIG. 7, comprising In FIGS. 7A and 7B, mean CSAs at four points in the respiratory cycle are presented for each dog before (hatched columns) and after (solid columns) administration of ritanserin. Asterisks highlight significant changes in airway size ($p<0.05$). FIGS. 7C and 7D depict the data presented in FIGS. 7A and 7B, respectively, as respiratory cycle loops of airway CSA before ritanserin administration (solid lines), and following ritanserin administration (hatched lines).

DETAILED DESCRIPTION

Figure 3A:
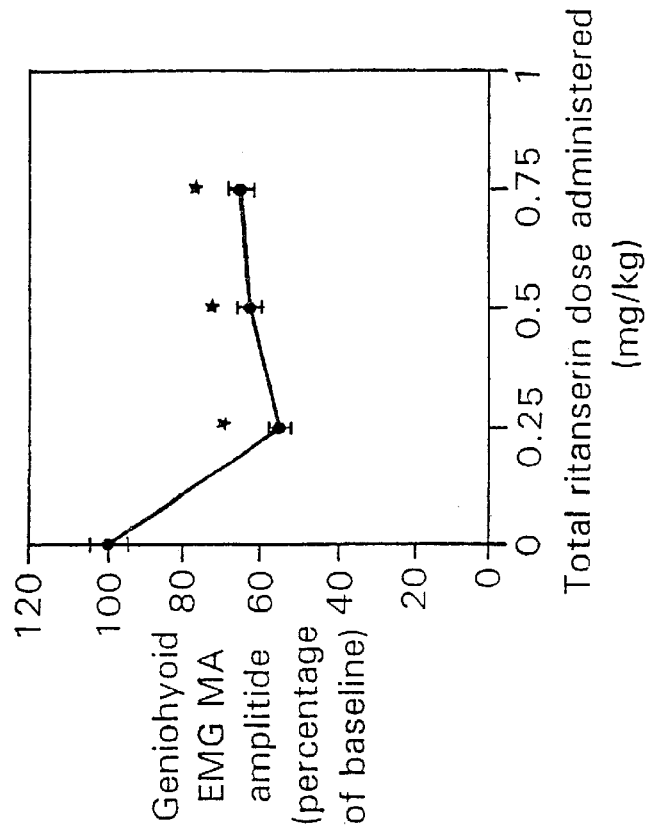
FIGS. 3A, 3B, 3C, 3D, 3E and 3F, is series of graphs which indicate the effects on upper airway dilator muscle activity of administering a serotonin antagonists to individual English bulldogs.

The invention relates to the discovery that disordered breathing episodes an be alleviated or prevented in a mammal such as a human or an English bulldog by administering a hypoglossal motoneuron-stimulating composition to the mammal.

The hypoglossal motoneuron-stimulating composition of the invention comprises a serotonin re-uptake inhibitor and at least one of a serotonin precursor and a serotonin agonist. The serotonin re-uptake inhibitor of the composition of the invention may, for example, be trazadone, fluoxetine, or nefazodone. The serotonin agonist of the composition of the invention may, for example, be serotonin, carboxamidotryptamine maleate (5-CT), or ± dimethoxy-4-iodoamphetamine (DOI). The serotonin precursor may, for example, be L-tryptophan or L-5-hydroxytryptophan. Although several of these compounds have been investigated as agents useful for treating disordered breathing, the use, in combination, of a serotonin re-uptake inhibitor and a serotonin precursor for this purpose has not been described by others. The composition of the invention may, of course, comprise all three of a serotonin re-uptake inhibitor, a serotonin precursor, and a serotonin agonist.

As used herein, the term "serotonin re-uptake inhibitor" means a composition of matter which, when administered to a mammal such as a human, inhibits active uptake of serotonin into a presynaptic neuron of a raphe nucleus of the mammal from the synaptic cleft between the presynaptic neuron and a hypoglossal motoneuron. By way of example, trazodone, fluoxetine, and nefazodone are serotonin re-uptake inhibitors.

As used herein, a "serotonin precursor" is a compound which, when administered to a mammal such as a human, is metabolized to yield serotonin as a final product or as an intermediate. Examples of serotonin precursors include L-tryptophan or L-5-hydroxytryptophan.

As used herein a "serotonin agonist" is a composition which, when provided to a serotonin receptor, activates the receptor.

Without wishing to be bound by any particular theory, it is believed that the serotonin re-uptake inhibitor enhances and extends the hypoglossal motoneuron-stimulating effect of serotonin which is normally released by serotonergic neurons of the raphe nuclei. While still not wishing to be bound by any particular theory, it is believed that the serotonin precursor of the composition of the invention prevents or reduces tachyphylaxis which is associated with administration of serotonin re-uptake inhibitors by preventing down-regulation of endogenous serotonin synthesis.

In one embodiment, the composition further comprises a thyrotropin-releasing hormone agonist. The TRH agonist of the composition of the invention may, for example, be TRH, montirelin, or CG-3703 (Itoh et al., 1995, J. Pharmacy Pharmacol. 47:833–836). Montirelin and a method of making montirelin are described, for example, in U.S. Pat. No. 4,045,556 to Schwertner et al.

As used herein, a "serotonin agonist" is a composition of matter which, when administered to a mammal such as a human, enhances or extends a biological activity attributable to the level or presence of endogenous serotonin in the mammal.

As used herein, a "TRH agonist" is a composition of matter which, when administered to a mammal such as a human, enhances or extends a biological activity attributable to the level or presence of endogenous TRH in the mammal.

The invention also includes a method of alleviating or preventing a disordered breathing episode, the method comprising administering the hypoglossal motoneuron-stimulating composition to a mammal which has experienced, which is experiencing, or which is imminently anticipated to experience such an episode. This method of the invention may be practiced by administering the composition of the invention together with a pharmaceutically acceptable carrier to a mammal such as a human.

As used herein, the term "pharmaceutically-acceptable carrier" means a chemical composition with which the composition of the invention may be combined and which, following the combination, can be used to administer the composition of the invention to a mammal.

The pharmaceutical compositions useful for practicing the invention may be administered to deliver a dose of each component of the composition of the invention between 1 ng/kg/day and 100 mg/kg/day.

Pharmaceutical compositions that are useful in the methods of the invention may be administered systemically in oral solid formulations, ophthalmic, suppository, aerosol, topical or other similar formulations. In addition to the composition of the invention, such pharmaceutical compositions may contain pharmaceutically-acceptable carriers and other ingredients known to enhance and facilitate drug-administration. Other possible formulations, such as nanoparticles, liposomes, resealed erythrocytes, and immunologically based systems may also be used to administer the composition of the invention according to the methods of the invention.

Exemplary compositions and doses of the composition of the invention include the following. The composition may be administered in a form to provide about 3.3 milligrams of trazodone and about 44.3 milligrams of L-tryptophan per kilogram of body weight to the mammal. The composition may be administered in a form to provide about 6.7 milligrams of trazodone and about 89.0 milligrams of L-tryptophan per kilogram of body weight to the mammal, Further by way of example, the composition may be administered in a form to provide about 13.3 milligrams of trazodone and about 178.3 milligrams of L-tryptophan per kilogram of body weight to the mammal. L-tryptophan may be administered, for example, in the form of a gel capsule. Trazodone may be administered, for example, in the form of a solution of trazodone in dimethyl sulfoxide (DMSO).

As used herein, a "disordered breathing episode" is a sleep state-dependent loss of upper airway patency in a mammal such as a human. By way of example, a loss of upper airway patency associated with obstructive sleep apnea results in a disordered breathing episode.

As used herein, a mammal is "imminently anticipated" to experience a disordered breathing episode if the mammal is known to have experienced, in the past, a disordered breathing episode associated with a physiological state such as sleep and if it is known or believed that the mammal will experience the same physiological state in the immediate future, such as within the ensuing twenty-four, twelve, six, or preferably two hours.

As used herein, a disordered breathing episode is "alleviated" if the severity of a symptom of the episode is reduced.

Conditions associated with disordered breathing episodes include, but are not limited to, snoring, hypopneas, apneas, obstructive sleep apnea, sleep hypopnea syndrome, upper airway resistance syndrome, and severe snoring conditions associated with arousal from sleep. All of these phenomena are characterized by recurrent nighttime arousal and sleep fragmentation. In addition, treatment of conditions such as hypersomnolence, which have a physiological presentation related to sleep apnea, but which do not involve sleeping per se, are also included in the invention. The compositions and methods of the invention may be used to alleviate or prevent any of these conditions.

The invention further relates to a kit comprising the composition of the invention, either in the form of a single composition of matter or as a package comprising a plurality of compositions which together include a serotonin re-uptake inhibitor and an agent selected from the group consisting of a serotonin precursor and a serotonin agonist The kit of the invention may, for example, comprise a serotonin re-uptake inhibitor such as trazodone in the form of a sterile injectable solution and a serotonin precursor such as L-tryptophan in the form of an orally administrable gel capsule. The kit of the invention may further comprise an instructional material which describes administration of the serotonin re-uptake inhibitor of the kit and the agent of the kit for the purpose of alleviating or preventing a disordered breathing episode in a mammal such as a human.

As used herein, an "instructional material" includes a publication, a recording, a diagram or any other medium of expression which can be used to communicate the usefulness of the composition of the invention for communicate the usefulness of the composition of the invention for alleviating or preventing a disordered breathing episode in a mammal such as a human. The instructional material of the kit of the invention may, for example, be affixed to a container which contains one or more components of the composition of the invention or be shipped together with a container which contains the composition. Alternatively, the instructional material may be shipped separately from the container with the intention that the instructional material and the composition of the invention be used cooperatively by the recipient.

The mammal which is treated using the compositions and methods of the invention may be any mammal, it being understood that substantially all mammals possess serotonergic neurons of the raphe nuclei which interact with hypoglossal motoneurons in a consciousness-dependent manner. Preferably, the mammal is a human.

The invention is further described in detail by reference to the following experimental examples. These examples are provided for the purpose of illustration only and are not intended to be limiting unless otherwise specified. Thus, the invention should in no way be construed to be limited to the following examples, but rather, should be construed to encompass any and all variations which become evident as a result of the teaching provided herein.

EXAMPLE 1

Pharmacotherapeutic Efficacy of Serotonergic Compounds for Treating Sleep Apnea in Bulldogs In the experiments described in this Example, the efficacy of the compositions and methods of the invention is demonstrated.

The efficacy of using serotonergic compositions to treat sleep apnea in bulldogs was examined using a composition comprising trazodone and L-tryptophan. Trazodone is a powerful serotonin re-uptake inhibitor. A product of physiological trazodone metabolism is known to have an excitatory effect at motoneurons having type 2C receptors, and thus may be termed a $5HT_{2C}$ agonist (Curzon et al., 1990, TIPS 11:181).

The advantages of performing the present studies in the English bull dog are as follows. This animal model exhibits the major clinical features of the sleep apnea syndrome and, thus, enables the study of multiple trials at multiple doses to provide insight into optimal dosing and individual response. Multiple studies can be performed at baseline, thereby providing a powerful analysis of the effects of drugs on the clinical features of the sleep apnea syndrome. Implanted electrodes provide quality EEG signals for accurately determining sleep state and quality EMG signals for assessing the effect of a drug on upper airway muscle activity. Detailed radiographics provide insights into the mechanical impact of sleep apnea-affecting drugs on upper airway function. Arterial pressure telemetry facilitates insight into the effects of sleep apnea on blood pressure and the effects of treatment on blood pressure during sleep and awakening.

The materials and methods used in the experiments presented in this Example are now described.

Surgical Procedures

Two telemetry devices were implanted in each of four English bulldogs. One of these devices allowed long-term measurement of electroencephalography (EEG) and electromyography (EMG) of an upper airway dilator muscle, the sternohyoid. The second device measured blood pressure. The surgical procedures were as follows.

Each dog was pre-medicated with 0.005 milligrams per kilogram body weight of atropine sulfate administered intramuscularly and general anesthesia was induced with intravenously-administered thiopental (25–35 milligrams per kilogram body weight). The dogs were endotracheally intubated and general anesthesia was maintained with inhalational isofluorane (1–2.5% v/v).

A midline 8-centimeter suprascapular incision was made in each dog and a subcutaneous pocket with a 10 centimeter diameter was created. A second incision (3 centimeters in diameter) was made in the midline dorsal neck of each dog. A scalp incision (midline 8 centimeters) was made to expose the skull. An electrode telemetry transmitter (TL10M3 Bioimplant, Data Sciences, Minnesota) was placed into the suprascapular pocket, and the electrodes of the unit (2 EEG, 1 ground, 2 sternohyoid EMG and 2 nuchal EMG electrodes) were urged subcutaneously to the neck incision The 2 EEG and the ground electrodes were then tunneled to the scalp incision, where a 4 by 4 centimeter surface of the fronto-parietal skull was cleared of its periosteum and thoroughly dried. Two stainless steel screw skull EEG electrodes were secured into the skull, each being positioned 1 centimeter from the midline. A third screw electrode, serving as the ground electrode, was placed 3 centimeters caudal to the EEG electrodes. These screw electrodes were covered with dental acrylic to fix the electrodes securely to the skull. Once the acrylic had dried, the scalp incision was sutured closed.

Two nuchal EMG electrodes were sutured into the dorsal neck musculature. A 6-centimeter incision was made as a midline ventral neck incision over the basohyoid bone to expose the sternohyoid (GH) muscles. Each of the two upper airway electrodes, passed from the neck incision, were sutured into one of the SH muscles. The dorsal and ventral neck incisions were sutured, and the intrascapular incision was sutured.

The animal was allowed to arouse spontaneously from anesthesia, and once alert, was extubated. Provided that the dog's post-operative course was uneventful, the dog was returned to its home cage five hours after surgery. Post-operatively, the dogs were monitored daily for signs of infection. Sutures were removed seven days after surgery.

Recording Procedures and Signal Processing

All sleep studies were conducted on the dogs in a 64 cubic foot well-ventilated Plexiglas recording chamber in a sound-attenuated room. Recording was conducted after at least one week following surgery; each of the animals had spent one week habituating to the recording chamber (daily nap sessions in the chamber).

Just before each study commenced, an ear oximeter was attached to the dog's pinna and oximetry was measured continuously using a Biox IIA oximeter (Ohmeda, Boulder, Colo.). Inductive plethysmographic bands (Respitrace®; Ambulatory Monitoring, Ardsley, N.Y.) were secured to the dog's chest wall and abdomen to measure respiratory movements. Airflow was assessed using thermistors (Easy Flow, EPM Systems, Midlotian, Va.), and snoring was assessed using a snore sensor obtained from the same company. A receiver (RLA2000, Data Sciences) was attached to the top of each recording chamber.

The signals for EEG, nuchal EMG, and sternohyoid EMG from the receiver were transmitted to a Receiver multiplexor (RMX 10, Data Sciences). These electrical signals were amplified and band-pass filtered at 1–100 Hertz (EEG) and 50–100 Hertz (EMG) using a low-noise amplifier (CWE, Inc., Ardmore, Pa.). The SH EMG signal was passed through a moving averager (CWE MA) having a time constant of 100 milliseconds. All processed signals were passed both directly to a polygraph and, through an analog-to-digital converter (UA10, Univ Analog Adapter, Data Sciences), to a computer which was operating the WINDAQ IBM AT computer-based data acquisition and analysis software package (EX Software and Adv CODASS, Dataq, Akron, Ohio).

All signals were stored digitally using a videotape recorder (Instrutech, Minneola, N.Y.) and as analog signals using a chart recorder (Gould TA2000) to display the signals for EEG, nuchal EMG, SH EMG, SH EMG moving average, airflow, the snore sonogram, and the rib cage and abdominal plethysmography. $SaO_2$ values were continuously recorded on the polygraphic records.

Data Processing.

SH MA, rib cage and abdominal plethysmographic signals, and airflow signals were processed using the WINDAQ software package at a sampling rate of 1000 measurements per second to score sleep-disordered breathing events. The investigator who assessed various events was blinded to the condition being tested during all trials. Sleep stages were scored from the polygraphic records using standard criteria (see, e.g., Rechtschaffen et al., 1968, *A Manual of Standardized Terminology, Techniques and Scoring System for Sleep Stages of Human Subjects*, UCLA Brain Information Service/Brain Research Institute, Los Angeles, Calif.). To determine the percentage of suppressed bursts (defined as bursts with peak amplitudes less than half the mean value in the preceding waking minute), the moving average signal was passed through the WINDAQ software package. In addition, this software package provided a frequency distribution of percent reductions in upper airway muscle activity for all bursts in each sleep stage during each of the four conditions.

Data analysis and Interpretation.

Sleep stages were defined as follows: (i) waking: high frequency, low amplitude EEG associated with neck EMG activity and eye movements (these were readily observed on skull EEG electrode recordings); (ii) non-REM sleep: slow wave high amplitude EEG without eye movements and some tonic neck EMG activity; (iii) REM sleep: high frequency low voltage EEG with bursts of more than five eye movements within four seconds and no tonic neck EMG activity, but some phasic neck activity.

The objective measures which were recorded were as follows: (1) sleep-disordered breathing index (SDBI), expressed as events/hour, (2) Percentage of hemoglobin oxygen saturation ($SaO_2$), expressed as a mean value for each behavioral state and the average nadir in sleep-disordered breathing events; (3) sleep architecture, including sleep latency, efficiency, and distribution of behavioral states; and (4) geniohyoid activity, as described herein.

Each dog participated in four baseline sleep studies and sixteen experimental sleep studies during which one of the following compositions was administered to the animal: Composition (1): Placebo/Vehicle; Composition (2) 3.3 mg/kg (trazodone) and 44.3 mg/kg (L-tryptophan); Composition (3) 6.7 mg/kg (trazodone) and 89.0 mg/kg (L-tryptophan); Composition (4) 13.3 mg/kg (trazodone) and 178.3 mg/kg (L-tryptophan). The sixteen experimental studies were evenly divided among the four compositions. Owing to the dose sizes and the poor solubilities of the compounds, L-tryptophan was administered orally in the form of a gel capsule and trazodone was administered intravenously in the form of a solution in DMSO.

Repeated measures analysis of variance (ANOVA) was used to compare results of the objective observations made during each of the four types of sleep study. Individual ANOVAs were performed using this technique to show individual responders to therapy. The percent reduction in SDBI necessary to define responsiveness to drug for each dog (coefficient of variation) was determined from vehicle sleep studies. This value, coupled with the repeated-measures ANOVA, provided a careful statistical analysis. ANOVA was also used to evaluate group response to drug administration by assessing the group response for each drug level relative to the baseline following administration of vehicle. In each case, the validity of the ANOVA model was assessed by examining plots of the standardized residuals. Transformations of values was used to normalize the residuals, if necessary. If an appropriate transformation was not possible, the data were analyzed using a non-parametric analysis, namely the Wilcoxon signed rank test for frequency-distribution studies and the Wilcoxon rank sum test to analyze group changes.

The results of the experiments presented in this Example are now described.

The use of a serotonin re-uptake inhibitor alone is not effective for long-term treatment of sleep apnea or other conditions associated with disordered breathing episodes. This is so because chronic use of serotonin re-uptake inhibitors leads to down-regulation of serotonin synthesis by the presynaptic neurons. Prolonged administration of a serotonin re-uptake inhibitor, such as daily administration for more than two weeks leads to tachyphylaxis, whereby further administration of the serotonin re-uptake inhibitor has severely reduced or no physiological effect. Serotonin synthesis is directly related to the amount of the biosynthetic precursor L-tryptophan that is available. Therefore, it was hypothesized that administration of a serotonin precursor such as L-tryptophan or L-5-hydroxytryptophan together with a serotonin re-uptake inhibitor would prevent the down regulation of the serotonin synthesis and the attendant tachyphylactic effect.

Administration of the composition of the invention, at each of the doses studied, had no effect on sleep latency. A significant dose-dependent increase in sleep efficiency ($p<0.025$) was associated with administration of the composition at each dose level. Significant dose-dependent reductions in the arousal index ($p<0.05$) and in NREMS RDI ($p<0.05$), was associated with administration of the composition at each dose level. A significant reduction in the REMS RDI was observed using composition dose level 4 ($p<0.01$). Furthermore, a significant reduction in the percentage of sleep time during which oxyhemoglobin was desaturated was observed at composition dose levels 3 and 4 ($p<0.05$).

EXAMPLE 2

The Importance of Serotonin for Maintenance of Airways and Normal Respiration During Waking in Patients Afflicted with Obstructive Sleep Apnea In the experiments described in this Example, two serotonin antagonists were evaluated for their effects on upper airway dilator muscle activity, diaphragm activity, oxyhemoglobin saturation ($SaO_2$), and upper airway cross-sectional area in English bulldogs. The serotonin antagonists which were evaluated were methysergide, a broad spectrum serotonin antagonist, and ritanserin, a more specific antagonist of serotonin receptor subtypes IC and 2.

The materials and methods used in the experiments presented in this Example are now described.

Subjects

Eight adult English bulldogs weighing 14 to 24 kilograms each were studied. The dogs were housed individually and maintained on a 14:10 hour light:dark cycle wherein the lights were switched on at 8:00 am. Food and water were provided ad libitum.

To document the presence of sleep-disordered breathing, each dog underwent a baseline sleep study consisting of one three- to seven-hour nap session. In this breed of dog, this nap period typically allows the study of two complete sleep cycles. Prior to the study, each dog had been acclimated to the recording chamber for at least several weeks, so that all dogs had slept many times within this chamber.

Objective measures for the sleep studies included measurement of oxyhemoglobin saturation during sleep and calculation of each dog's sleep-disordered breathing index during REM sleep. Oxyhemoglobin saturation was measured using a Biox II oximeter (Ohmeda, Boulder, Colo.) secured to the dog's pinna. Respiratory movements of the rib cage and abdomen were measured by impedance plethysmography (Respitrace®; Ambulatory Monitoring, Ardsley, N.Y.). The degree of respiratory disturbance during sleep was calculated for each dog using methods previously described for the English bulldog (Hendricks et al., 1987, J. Appl. Physiol. 163:1344–1350). Sleep-disordered breathing events were defined as conditions during which a desaturation in oxyhemoglobin by at least 4% and either a reduction in rib cage plethysmographic respiratory motion by more than 30% from measures obtained in the preceding thirty seconds or paradoxical movements of the chest and abdominal plethysmograms were observed. Sleep-disordered breathing events were expressed as the number of events per hour of REM sleep.

For these studies, behavioral states were defined as follows: Quiet waking (QW) was defined as the presence of open eyes, a responsiveness to the environment, and a sitting or recumbent posture. Non-REM sleep was defined by the presence of prone recumbent posturing, closed eyes, an unresponsiveness to environment, and an absence of both ear and extremity twitches. REM sleep was defined by a prone recumbent posturing, an unresponsiveness to environment, and paroxysms of ear or extremity twitches. Previous experience with the English bulldogs indicated that the above behavioral definitions are in agreement with standard electrophysiologic definitions of sleep states. Further, any portion of the sleep study for which a behavioral state could not readily be defined was not analyzed.

Surgical Procedures

Following the baseline sleep study to document sleep-disordered breathing, each dog underwent a surgical procedure for the implantation of recording electrodes. For this procedure, dogs were premedicated with 5 to 10 micrograms per kilogram body weight atropine sulfate intramuscularly. In the cases of two bulldogs experiencing severe sleep-disordered breathing, intubation and general anesthesia were thought to pose a significant risk for postoperative respiratory failure. These two dogs were therefore sedated only using 20 to 40 micrograms per kilogram body weight oxymorphone administered intramuscularly. The six remaining dogs were anesthetized initially with sodium thiopental (15 to 30 milligrams per kilogram body weight) administered intravenously. The dogs were intubated and maintained under general anesthesia using 0.5 to 2.5% (v/v) inhalational halothane throughout the procedure.

Recording electrodes were implanted for the study of diaphragm and upper airway dilator muscle activity. Electrodes were fashioned from 0.7 millimeter multi-stranded Teflon-coated stainless steel wire. The insulation was stripped from 5 to 8 millimeters at the proximal tip. The proximal tip of each electrode was implanted transcutaneously into the relevant musculature using methods described by Basmajian et al. (1962, J. Appl. Physiol. 17:839).

Five diaphragm electromyographic (DIA EMG) electrodes were implanted in the costal musculature of the right hemidiaphragm 7 to 9 centimeters lateral to the xyphoid process. Three other electrodes were embedded into the right sternohyoid (SH) muscle and, three more were embedded into the right geniohyoid (GH) muscle. Both SH and GH muscles are readily palpable in the English bulldog. Previous studies have shown comparable recordings from transcutaneously placed electrodes and from electrodes placed under direct visualization of the muscles (Hendricks et al., 1991, Am. Rev. Respir. Dis. 144:1112–1120).

Two ground electrodes were embedded transcutaneously contacting both the occipital skull and dorsal neck musculature. Distal tips of all electrodes were soldered onto a 25-pin Winchester-type connector. Electrodes and the connector were secured to each dog with elastic adhesive dressings over the torso and neck.

No dog exhibited signs of discomfort or changes in behavior after recovery from either anesthesia or sedation with analgesia. Once fully alert following anesthesia, each of the six dogs given general anesthesia was allowed 24 hours of rest in its home cage prior to the commencement of the study. The two dogs receiving oxymorphone were fully alert one hour after oxymorphone injection, and were allowed four hours of recovery prior to the study.

Electrophysiologic Recording Procedures

All studies were conducted using an unrestrained dog, either housed within a well-ventilated, electronically shielded, clear Plexiglass™ recording chamber or seated atop a table in the recording room. In either case, an investigator remained with the dog throughout the study to observe the dog's head and neck movements and to document the behavioral state of the dog. EMG signals were band-pass filtered at 50 to 2,000 Hertz. DIA EMG signals were passed through an analog EKG blanker (CWE EKG blanker; CWE, Ardmore, Pa.) and then through a third-order Paynter filter (CWE MA) having a 100-millisecond time constant to obtain a moving average of the DIA EMG. Signals of the SH and GH EMG were also passed through Paynter filters with the same time constants (100 ms) to obtain moving averages of these signals. Oxyhemoglobin saturation was measured continuously with a Biox IIA oximeter attached to the dog's pinna. Signals for the GH EMG, GH moving average (MA), SH EMG, SH MA, DIA EMG, DIA MA, and oxyhemoglobin saturations were recorded polygraphically (10 millimeters per second) using a chart recorder with high frequency response, i.e., as much as 10 kHz (Gould ES1000; Gould Instruments, Cleveland, Ohio). Signals were also recorded on analog tape using an eight-channel FM tape recorder (A. R. Vetter, Roseburg, Pa.).

Study Protocol

The effects of serotonin antagonists on upper airway dilator muscle activity and breathing during wakefulness were assessed. Serotonin antagonists which were administered were methysergide maleate and ritanserin. Both serotonin antagonists readily cross the blood brain barrier (Bredberg et al., 1990, Dispos. Biol. Fate Chem. 18:336–343; Devaud et al., 1992, J. Neurochem. 59:1459–1466).

Methysergide is a nonspecific broad-spectrum serotonin antagonist with greatest affinity for serotonin type 2F receptors (Bredberg et al., supra). Methysergide has been shown to suppress both hypoglossal and trigeminal motoneuronal activity in cats when injected into the relevant motoneuronal pools (Ribiero-do-Vale et al., 1991, Brain Res. 550:197–204; Kugin, 1992, Neurosci Lett. 139:243–248).

Ritanserin is a relatively selective serotonin antagonist at types 1C and 2 serotonin receptors (Devaud et al., 1992, J. Neurochem. 59:1459–1466). Ritanserin was selected for study on the basis that the IC and 2 subtypes of serotonin receptors appear to be involves in serotonin facilitation of hypoglossal motoneurons in vivo (Kugin et al., supra). Although the effects of ritanserin on upper airway motor activity have not been studied, another serotonin antagonist selective for receptor subtypes 1 C and 2, namely ketanserin, has been demonstrated to depress hypoglossal motoneuronal activity when microinjected into the hypoglossal motor nucleus (Kugin et al., supra). However, ketanserin exhibits activity as an alpha-1-adrenoreceptor antagonist in addition its serotonin blocking activity (Koss, 1991, Eur. J. Pharmacol. 194:161–166). The drugs studied in the experiments described in this Example were dissolved in warmed saline at a concentration of 1 milligram per milliliter, and 0.5 microliters of HCl was added per 50 milliliters of saline if necessary to fully dissolve either drug.

After obtaining baseline recordings of all variables for at least 5 minutes during quiet wakefulness and after obtaining recordings during the 5 minutes following administration of a saline control injection, 0.25 to 0.50 milligrams per kilogram body weight of one of the serotonin antagonists was administered to each dog through a peripheral intravenous line. All variables were continuously recorded. Injections were repeated every 6 minutes either until a total dose of 1 milligram per kilogram body weight had been administered or until the oxygen saturations fell below 85%. These limits were deemed to ensure the dogs' safety, based on an initial study using one dog. This dog, EBD-G was hypoxic at baseline and developed profound reductions in UAW muscle activity with desaturations to 75% after a total dose of 1.0 milligram per kilogram body weight of methysergide. The interval between repeated injections was selected to be 6 minutes to allow for 5 minute sampling periods for each dose. The duration of action of serotonin antagonists is known to be greater than 60 minutes (Bredberg et al., supra; Devaud et al., supra).

The behavior of the dogs was observed directly throughout this study and for several hours following the last injection by one investigator seated adjacent the dog. The investigator documented both behavioral state and movement and helped the dog to maintain wakefulness throughout the study.

Imaging of the Upper Airway

The effect of administering a serotonin antagonist on upper airway dimensions during a respiratory cycle was determined by performing cinematic computed tomography (cine CT) on dogs before and after administration of the antagonists. Cine CT allows both high spatial and temporal resolution (Shepard et al., 1990, In: *Proceedings of the First International Symposium on Sleep and Respiration*, New York, 273–282; Schwab et al., 1993, Am. Rev. Respir. Dis. 148:1385–1400), and has been used to define dynamic changes in the upper airways of humans in relation to the phases of the respiratory cycle (Schwab et al., 1993, Am. Rev. Respir. Dis. 148:1385–1400; Galvin et al., 1989, Radiology 171:775–778; Schwab et al., 1993, J. Appl. Physiol. 74:1504–1514). An Imatron C-100 ultrafast scanner (Imatron Inc., South San Francisco, Calif.) was used for these studies.

Dogs were studied during wakefulness. All dogs were trained prior to the study to lie quietly on a table similar to the CT scanner table for periods as long as one hour. However, to maintain constant head and body position throughout the study, each dog wore a nylon vest secured to the table at the shoulder and hips. Lateral radiographs of the neck were performed initially so that the head and neck were positioned with a 110 to 130 degree angle between the hard palate and the upper trachea.

Once the angle was confirmed, the head was gently secured in place to the scanner table with elastic dressing tape. With the dog comfortably secured in place, a scout filming of the airways was performed with 40 consecutive 3-millimeter-thick coronal slices imaged from the region of the nasopharynx through the larynx. For each dog, these images were used to select four standard areas of study for all dogs. Despite anatomic differences between English bulldogs and humans, these four levels are comparable to levels studied in humans as described (Schwab et al., 1993, Am. Rev. Respir. Dis. 148:1385–1400). For each dog, the areas which were imaged included the posterior nasopharynx (at the level of pterygoid fossa in the dog), the retropalatal high area (at the midhyoid arch level), the retropalatal low area (at the level of the anterior hyoid bone), and the larynx.

Prior to imaging, each dog was connected as described above for monitoring geniohyoid, sternohyoid, and diaphragm muscle activity, respiratory inductive plethysmography, and oxyhemoglobin saturation. During quiet breathing, 20 consecutive images at 0.4-second intervals were obtained simultaneously at each of the four described levels. This program allowed for the description of the dynamic changes in airway dimensions over four to seven breaths at all four anatomic levels simultaneously. The image acquisition time for each radiograph was 50 milliseconds, and images were 3 millimeters thick. Imaging studies were rejected and repeated if the respiratory activity was interrupted at any time during imaging by swallowing, sighing (defined for this study as a diaphragm burst 200% greater in amplitude than the previous 10 bursts), licking, or panting, the latter being defined as a respiratory frequency of more than 60 diaphragmatic respiratory bursts per minute. Cine CT scanner impulses marking the timing for all images were transmitted to the polygraph with continuing signals of all objective measures, i.e., GH, SH, and DIA EMG activity, oxyhemoglobin saturation, and chest wall plethysmography.

Once baseline image acquisition was complete, each dog received a selected dose of a serotonergic agent intravenously. Two minutes after drug administration, the four-level multislice scanning was repeated using an identical protocol to that described for baseline conditions. The behavior of the dogs was directly observed throughout the study.

Data and Statistical Analysis

The primary purpose of the data analysis was to determine the effects of ritanserin and methysergide on upper airway motor activity, oxyhemoglobin saturation, and upper airway cross-sectional area in relation to the respiratory cycle. The objective measures for this study were measures of GH and SH motor activity, DIA motor activity, mean oxyhemoglobin saturation, and, in the second protocol, upper airway cross-sectional areas at various levels and phases of respiration and chest wall respiratory movements.

GH and SH motor activities were measured using the EMG moving average signals. Peak amplitudes of all respiratory bursts were measured for each burst using methods previously described (Hendricks et al., supra). Briefly outlined, this method comprised using the moving average of the rectified EMG signal, the peak amplitude was measured as the amplitude (measured in arbitrary units) from the end-expiratory level to the amplitude of the maximal activity within a respiratory burst. Sample durations were 5 minutes for each condition, beginning either 1 minute after drug or saline administration or, for baseline measurements, 5 minutes prior to drug administration.

Mean amplitudes of peak motor activity were calculated for each upper airway dilator in each dog studied by averaging the results of measurements of all respiratory bursts within a 5 minute sampling period. For each dog, all EMG data for a specific muscle were rejected if the phasic respiratory activity for that muscle was not readily apparent such that the ratio of peak amplitude to tonic amplitude was, on average for the saline sample, less than 2:1. Individual bursts were excluded from analysis if the EMG pattern was not respiratory-related (e.g., swallowing, licking, chewing, barking, or sighing).

To determine individual responsiveness to the serotonin antagonists, individual ANOVA for each dog was performed, wherein baseline data was compared with data at each incremental dose administered to the particular dog. These data were analyzed as the percent suppression from baseline for each dose.

Group data for GH and SH motor activity were analyzed using repeated measures of ANOVA and Scheffe's F test for doses of 0.00, 0.25, 0.50, 0.75, and 1.0 milligrams per kilogram of body weight. Statistical analyses of group data are reported only for subject numbers greater than or equal to four.

The effects of serotonin antagonists on diaphragm activity were similarly analyzed. Briefly, the measures of diaphragm activity were the peak amplitudes for all respiratory bursts in each condition. These data were determined from the moving average signals for DIA EMG. Acquisition of these measures has also been previously described (Hendricks et al., 1991, Am. Rev. Respir. Dis. 144:1112–1120). Mean values across all respiratory bursts of a 5 minute sample period were determined for each dog, and these values were used to perform repeated measures of ANOVA comparing baseline values with post-administration values.

Respiratory timing variables were obtained from the DIA MA signals, using methods previously described to determine inspiratory time ($T_1$), expiratory time ($T_E$), total time of a respiratory burst ($T_{tot}$), and the duty cycle ratio ($T_1/T_{tot}$) (Hendricks et al., 1987, J. Appl. Physiol. 63:1344–1350; Hendricks et al., 1991, Am Rev. Respir. Dis. 144:1112–1120).

The effects of ritanserin and methysergide on oxyhemoglobin saturations were analyzed in a similar fashion; i.e., repeated measures of ANOVA for baseline and drug dose conditions. Oxyhemoglobin saturation was measured every 10 scans. These data were used to determine mean saturation during each 5 minute sampling period.

This study quantified the effects of the serotonin antagonist, ritanserin, on the cross-sectional area of the upper airway and its dynamic changes during the respiratory cycle. For analysis of these data, the images obtained were first categorized relative to four time points within the respiratory cycle: midinspiration, end-inspiration, midexpiration and end-expiration. A digitized DIA EMG signal was used for the determination of these time points using a Macintosh NX computer equipped with a laboratory control package (LabVIEW 2.0; National Instruments, Austin, Tex.). The computer synchronously received signals directly from the DIA EMG signal and from the scanner marking the time each image was obtained. These signals were also recorded polygraphically using the variables described above. All images obtained were archived and later reviewed to find comparable anatomic levels as defined by bony landmarks.

Polygraphic records of muscle activity were used to measure upper airway motor activity before and after ritanserin administration, as described herein. Imaging was repeated following several minutes of motor depression. Individual images were rejected if the upper airway motor activity resembled swallowing, licking, panting, respiratory pauses greater than 2 seconds, or sighs. If possible, imaging was repeated if nonrespiratory behavior occurred during scanning. Where possible, images were collected over four or more breaths. Data were analyzed for changes in upper airway size and dynamics only if at least four images were obtained for each time point in the respiratory cycle at comparable anatomic levels for both baseline and post-administration images. The thickness of each airway segment scanned was 3 millimeters.

To more accurately determine the average airway cross-sectional area (CSA) for each segment, an analytical software system VIDA (Volume Image Display Analysis) was used. The details of this software together with validation of the algorithms have been described (Schwab, 1993, J. Appl. Physiol. 74:1504–1514). The VIDA system semiautomatically determines edges between the airway and surrounding tissues, the circumference of the airway, and the CSA of the airway. For each of the four time points of the respiratory cycle, four measures of CSA at each of the four levels were made in each dog before and after drug administration. As a result, 128 images were analyzed per dog. The four CSA values for each point in the respiratory cycle at each level were averaged to compare a mean pre-administration airway CSA with a postdrug CSA for a given anatomic level and a given respiratory phase. Mean values were then compared as a group using repeated-measures ANOVA.

The results of the experiments presented in this Example are now described.

Baseline Sleep Study Results

Prior to trials with serotonin antagonists, all eight dogs underwent one sleep study, consisting of a 3 to 7 hour daytime nap session. The mean sleep latency for the dogs was 16.38±2.35 minutes (all values expressed as mean±standard error). The mean sleep disordered breathing index during REM sleep was 30.44 events/hour ±10 4.95. The mean $SaO_2$ across all dogs in waking was 92.38±0.98%. The mean $SaO_2$ during REM sleep was 86.75±1.05%, and the mean $SaO_2$ nadir during REM sleep was 77.63±2.11%. Individual data are presented for the eight dogs in Table 1.

TABLE 1

SLEEP VARIABLES FOR BULLDOGS INCLUDED IN THIS STUDY

| Dogs | SDBI (events/h) | Mean $SaO_2$ Waking (%) | Mean $SaO_2$ REM Sleep (%) | Mean Nadir $SaO_2$ REM Sleep (%) |
|---|---|---|---|---|
| EBD-A | 36.9 | 92 | 85 | 80 |
| EBD-B | 39.4 | 92 | 84 | 74 |
| EBD-G | 48.0 | 86 | 82 | 72 |
| EBD-H | 4.4 | 94 | 90 | 85 |
| EBD-J | 38.5 | 93 | 86 | 74 |
| EBD-M | 33.3 | 93 | 88 | 71 |
| EBD-P | 25.5 | 94 | 89 | 78 |
| EBD-S | 17.5 | 95 | 90 | 87 |

Definition of abbreviation: SDBI=sleep-disordered breathing index as defined herein.

One of these dogs (EBD-H) was only minimally affected. However, because sleep-disordered breathing is not observed at all in normal English bulldogs (Hendricks et al., 1987, J. Appl. Physiol. 63:1344–1350), this dog was included in the analyses. Inclusion of this dog allowed data collection in dogs having a range of sleep-disordered breathing from mild disease to more severe disease.

Effects of Serotonin Antagonists on the Behavior of English Bulldogs

Each dog remained in the same state of alertness, quiet wakefulness, throughout the saline control periods and all subsequent drug injection sampling periods. Head and neck movements were likewise similar in all sampling periods, with the exception that methysergide resulted in an increase in staring behaviors for several dogs. However, general head and neck positions did not differ between methysergide and saline treated animals.

Effects of serotonin Antagonists on Upper Airway Dilator Motor Activity Ritanserin data.

Of the six dogs in which telemetry devices were implanted for the study of the effects of ritanserin, four had adequate phasic GH EMG activity to enable determination of drug effects on GH motor activity. All four of these dogs received doses of 0.25, 0.50, and 0.75 milligram per kilogram of body weight of ritanserin. Two of these dogs received a total of 1.0 milligram per kilogram of body weight ritanserin, while the other two dogs were not administered the full 1 milligram per kilogram of body weight dose because of excessive oxyhemoglobin desaturation. Each of the four dogs individually demonstrated reductions in GH peak amplitudes by ANOVA ($p<0.05$).

Data obtained from individual dogs for GH peak amplitudes before and after ritanserin are presented in FIG. 1A. Collectively, the dogs demonstrated reductions in GH peak amplitudes for the three cumulative doses of ritanserin. The baseline mean amplitude was 11.86±2.17 (arbitrary units±standard error). The mean amplitude following administration of 0.25 milligram per kilogram of body weight ritanserin was 6.42±1.12. The mean amplitude following administration of 0.50 milligram per kilogram of body weight ritanserin was 7.23±2.01. The mean amplitude following administration of 0.75 milligram per kilogram of body weight ritanserin was 7.44±2.48. There were significant differences between the baseline and each of the three doses ($p<0.05$). Data for the group of four dogs expressed as a percentage of baseline GH peak amplitude are shown in FIG. 1B. Despite differences in GH peak amplitudes from baseline, there were no significant differences in the amounts of GH suppression caused by administration of any of the three doses of ritanserin which were studied Recordings of the SH EMG activity were obtained in three of the six dogs which were administered ritanserin. Three dogs each tolerated doses of 0.25, 0.50, and 0.75 milligram per kilogram of body weight, and one of these dogs also tolerated 1.0 milligram per kilogram of body weight ritanserin. All three dogs exhibited a significant reduction in SH amplitude following ritanserin administration ($p<0.05$). The values obtained for SH amplitudes were $14.41\pm3.93$ arbitrary units (mean±standard error) at baseline, $10.90\pm2.99$ arbitrary units following administration of 0.25 milligram per kilogram of body weight ritanserin, $9.08\pm1.32$ arbitrary units following administration of 0.50 milligram per kilogram of body weight ritanserin, and $7.43\pm0.55$ arbitrary units following administration of 0.75 milligram per kilogram of body weight ritanserin. Individual data are presented in FIG. 1C, and group data are presented in FIG. 1D.

Methysergide data.

Four dogs were studied following administration of methysergide. In three of the four dogs, GH recordings were unsuccessful, secondary to low phasic to tonic ratios of EMG activity. However, data were successfully obtained for SH peak amplitudes in all four dogs. The effects of two doses of methysergide on sternohyoid activity were studied, namely 0.50 and 1.0 milligram per kilogram of body weight methysergide. Each of the four dogs exhibited a significant reduction in SH peak amplitude, as illustrated in FIG. 1E. SH peak amplitudes were $5.75\pm0.18$ (arbitrary units±standard error) at baseline, $3.83\pm0.28$ arbitrary units following administration of 0.50 milligram per kilogram of body weight methysergide, and $2.77\pm0.38$ arbitrary units following administration of 1.00 milligram per kilogram of body weight methysergide (ANOVA, $p=0.006$). As a group, there were significant differences between baseline SH peak amplitudes and SH peak amplitudes following administration of 0.50 milligram per kilogram of body weight methysergide ($p<0.05$) and between baseline SH peak amplitudes and SH peak amplitudes following administration of 1.00 milligram per kilogram of body weight methysergide ($p<0.01$), as indicated in FIG. 1F. As with ritanserin, no significant dose effect was observed.

The Effects of Ritanserin on Diaphragm Motor Activity

Recordings of DIA EMG and DIA MA were made before and after administration of ritanserin to each of six dogs. Each dog received doses of 0.25, 0.50, and 0.75 milligram per kilogram of body weight ritanserin, and three of the dogs received cumulative doses of 1 milligram per kilogram of body weight ritanserin. Four of the six dogs exhibited a significant reduction in DIA peak amplitude following ritanserin administration, as assessed by individual ANOVA ($p<0.05$). In each of the other two dogs, the difference between baseline and post-administration DIA peak amplitude was not significant. Individual data are presented in FIG. 2A. For the group, the mean DIA peak was=$17.63\pm2.79$ (arbitrary units±standard error) at baseline, $15.03\pm2.45$ arbitrary units following administration of 0.25 milligram per kilogram of body weight ritanserin, $16.12\pm2.30$ arbitrary units following administration of 0.50 milligram per kilogram of body weight ritanserin, and $14.98\pm2.06$ arbitrary units following administration of 0.75 milligram per kilogram of body weight ritanserin. As a group, DIA peak amplitude following administration of either 0.25 or 0.75 milligram per kilogram of body weight ritanserin was significantly less than the baseline values ($p<0.05$). Expressed as a percentage of the baseline value, data for the three doses were as follows. Following administration of 0.25 milligram per kilogram of body weight ritanserin, DIA peak amplitude was ($85.76\pm3.30$) % of the baseline value. Following administration of 0.50 milligram per kilogram of body weight ritanserin, DIA peak amplitude was ($95.22\pm5.81$) % of the baseline value. Following administration of 0.75 milligram per kilogram of body weight ritanserin, DIA peak amplitude was ($87.33\pm5.18$) % of the baseline value. Repeated measures ANOVA of these data indicated that the only significant reduction from baseline was when a dose of 0.25 milligram per kilogram of body weight ritanserin was administered. The group data are presented in FIG. 2B.

The Effects of Methysergide on Diaphragm Motor Activity

DIA EMG signals were obtained from three of the four dogs studied in this protocol. Individually, two of the three dogs exhibited a significant reduction in DIA peak amplitudes following methysergide administration. Individual and group data are presented in FIGS. 2C and 2D, respectively. DIA peak amplitudes were $7.07\pm2.37$ arbitrary units (mean±standard error) at baseline, $4.74\pm0.25$ arbitrary units following administration of 0.50 milligram per kilogram of body weight methysergide, and $2.80\pm1.48$ arbitrary units following administration of 1.0 milligram per kilogram of body weight methysergide. Expressed as a percentage of baseline DIA peak amplitude, DIA peak amplitude following administration of 0.50 milligram per kilogram of body weight methysergide 67.7% of the baseline value, and 39.6% of the baseline value following administration of 1.0 milligram per kilogram of body weight methysergide.

Suppression of Diaphragm versus Upper Airway Motor Activity

Figure 3B:
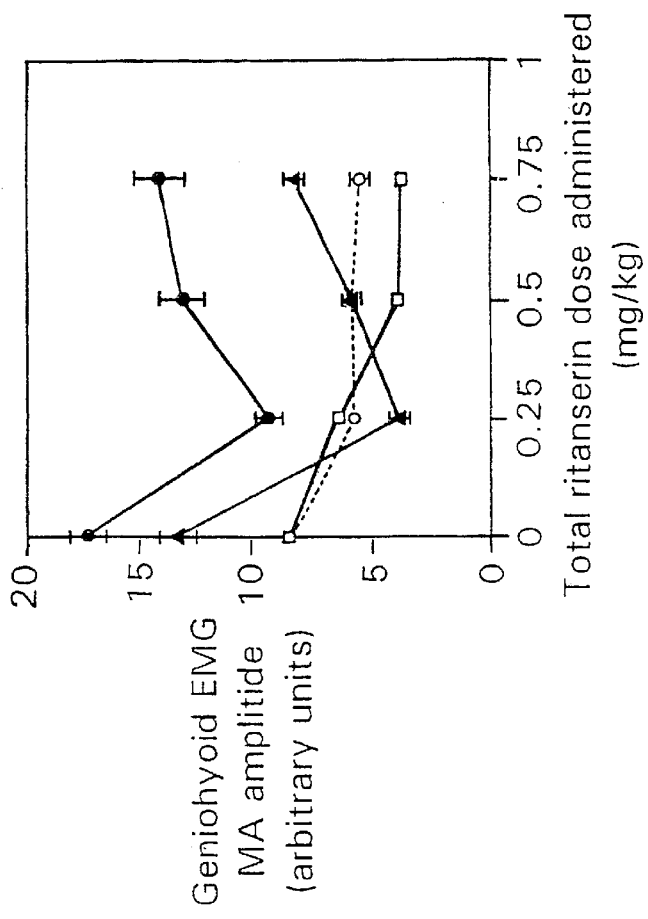
Figure 3D:
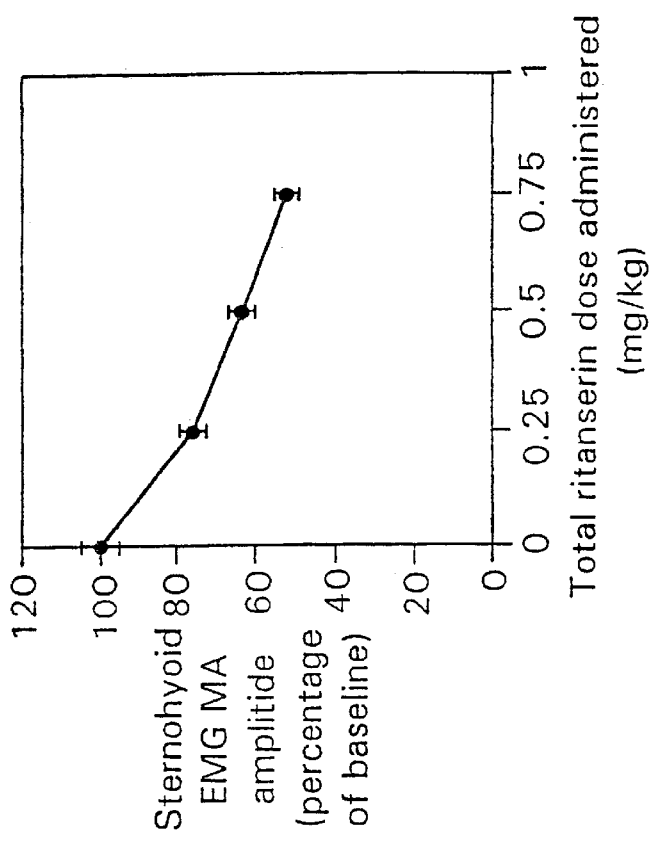
Figure 3C:
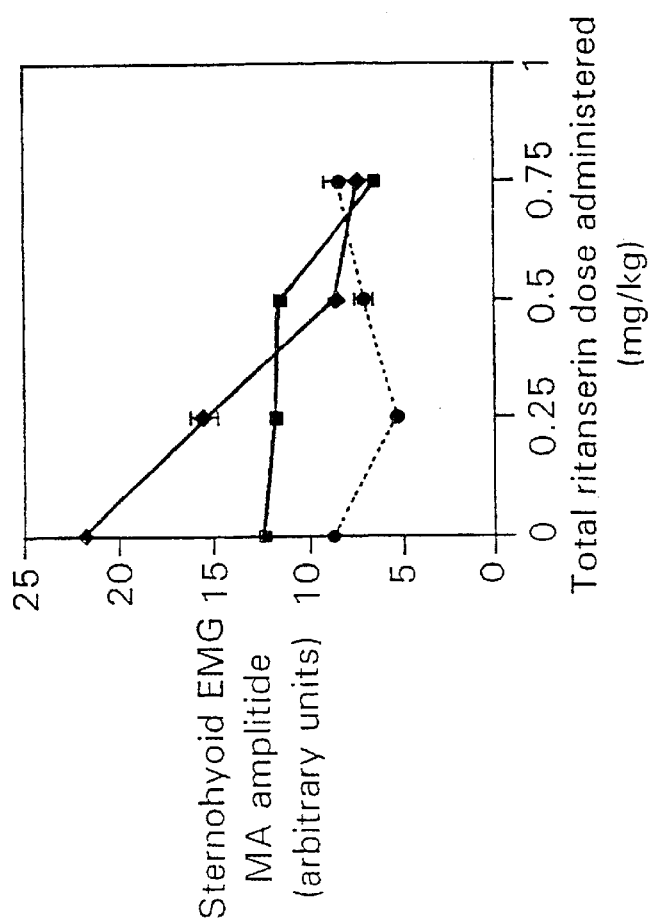
Figure 3F:
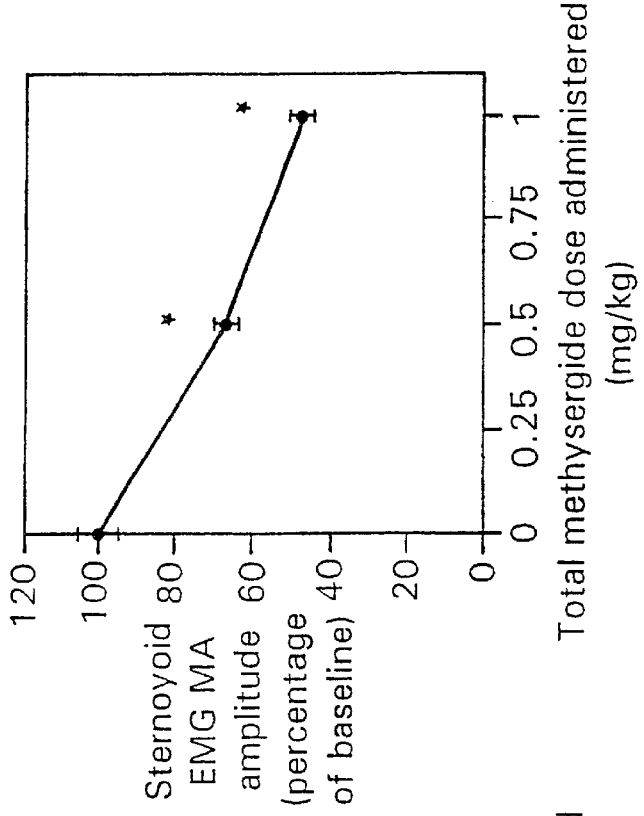
Figure 3E:
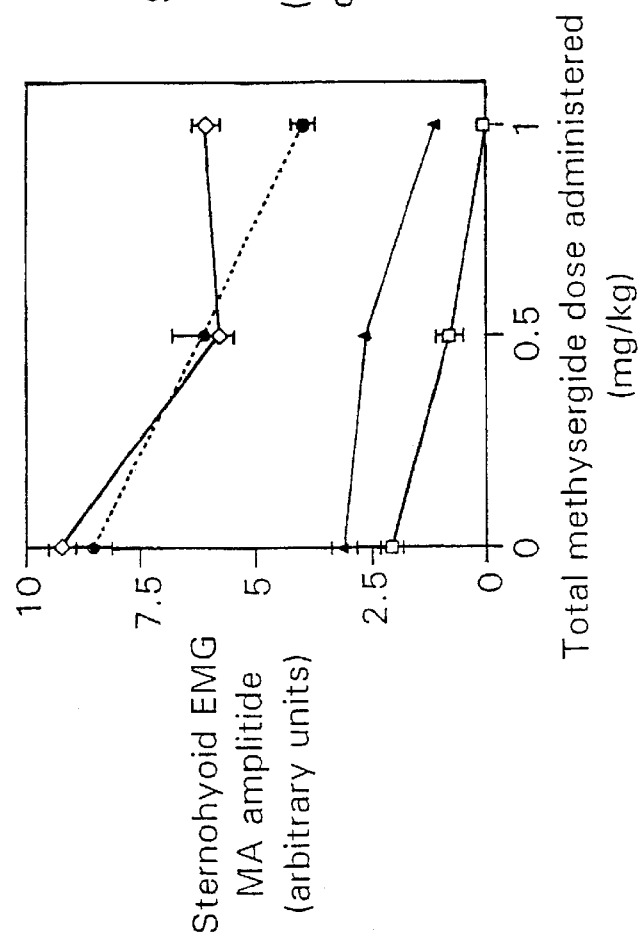

To determine if systemic administration of a serotonin antagonist during quiet waking would result in a greater suppression of upper airway motor activity than of diaphragm activity, the percent suppression of upper airway motor activity or the percent suppression of diaphragm activity was assessed collectively and in individual dogs. For statistical analysis, ritanserin data for GH and DIA obtained at a dose of 0.25 milligram per kilogram of body weight of the antagonist were used. Ritanserin suppressed GH activity by $40.0\pm6.5\%$ (mean±standard error) and suppressed DIA activity by $17.0\pm3.6\%$ ($p<0.05$). Three dogs exhibited adequate SH and DIA EMG phasic activity during methysergide trials. The percent suppression of SH and DIA was compared in dogs administered a 0.50 milligram per kilogram of body weight dose of methysergide. Individual data for percent suppression of muscle activity for both serotonin antagonists are presented in FIGS. 3A and 3B, showing individual percent suppression for GH and DIA in the four dogs receiving ritanserin and percent suppression of SH and DIA for the three dogs receiving methysergide.

One dog (EBD-G) exhibited a high DIA suppression and was hypoxic at baseline (resting $SaO_2=84$ to 87%). In addition, this dog demonstrated the most severe sleep-disordered breathing, as assessed by the frequency of S.B. events and mean SaO2 values during REM sleep, as indicated in Table 1. One bulldog (EBD-J) receiving both ritanserin and methysergide and exhibited comparable suppression following administration of either drag.

The Effects of S-HT Antagonists on $SaO_2$

Figure 4D:
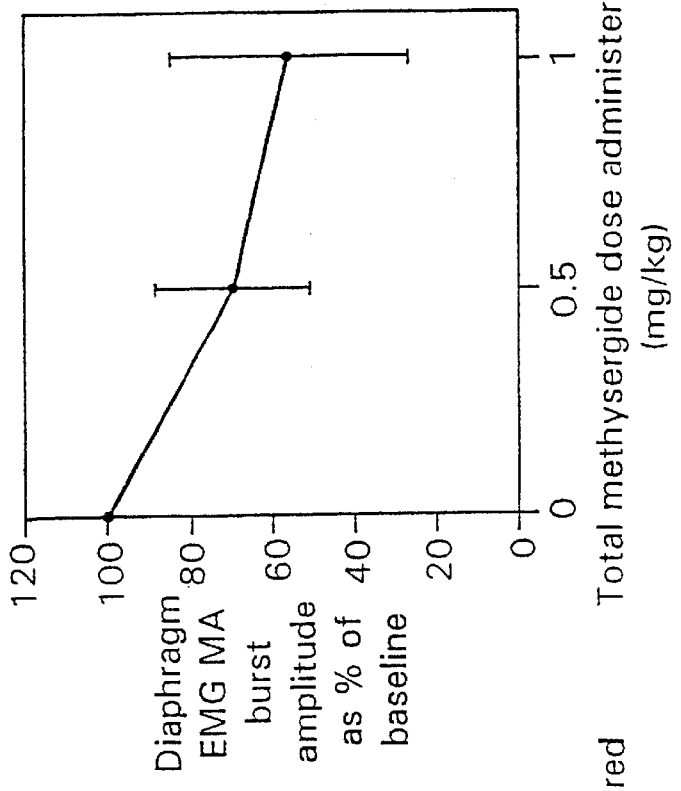
Figure 4C:
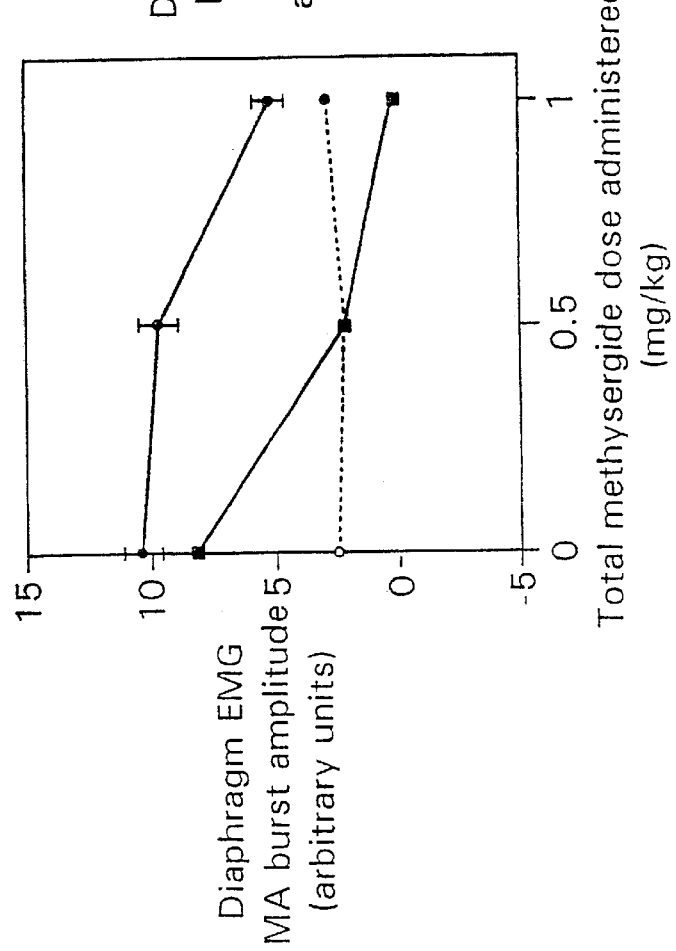

Oxyhemoglobin saturation ($SaO_2$) was analyzed to detect changes in mean saturation throughout each sampling period. Ritanserin data were recorded for all six dogs tested. For the group, mean $SaO_2$ was ($92.1\pm0.6$)% (mean±standard error) at baseline. Mean $SaO_2$ following administration of 0.25 milligram per kilogram of body weight ritanserin was ($88.5\pm0.8$)%. Mean $SaO_2$ following administration of 0.50 milligram per kilogram of body weight ritanserin was ($87.6\pm1.2\%$), and was ($88.6\pm0.5$)%, following administration of 0.75 milligram per kilogram of body weight ritanserin. For each ritanserin dose, the reduction in $SaO_2$ from baseline was significant ($p<0.05$). These data are summarized in FIG. 4. $SaO_2$ was measured for all four dogs during the methysergide trials. Mean $SaO_2$ was (90.3±2.7)% at baseline, (86.6±2.0)% following administration of 0.50 milligram per kilogram of body weight methysergide, and (85.6±0.9)% following administration of 1.0 milligram per kilogram of body weight methysergide. There was a significant difference between baseline $SaO_2$ and that following administration of 1.0 milligram per kilogram of body weight methysergide (p<0.05).

Effects of serotonin Antagonists on Respirator Timing

The effects of serotonin antagonists on respiratory timing were examined, specifically on $T_I$, $T_E$, $T_{tot}$ and $T_I/T_{tot}$. Because dose-related effects of serotonin antagonists on respiratory motor activity in the range of doses used were not observed, the effects of ritanserin on timing variables were analyzed only in using a dose of 0.25 milligram per kilogram of body weight. These values are presented in Table 2 for the six dogs studied. As indicated, there were significant reductions in $T_I$, $T_E$ and $T_{tot}$, without a change in the $T_I/T_{tot}$. For the three dogs studied which were administered 0.50 milligram per kilogram of body weight methysergide, $T_I$ was reduced by 12.7%, $T_E$ by 33.8%, and $T_{tot}$ by 23.9%, and $T_{tot}$ was increased by 17.3%.

TABLE 2

THE EFFECTS OF RITANSERIN ON RESPIRATORY TIMING*

|  | Baseline Values | Ritanserin Values (0.25 mg/kg) | p Value |
| --- | --- | --- | --- |
| $T_I$ | 1.31 ± 0.20 | 1.03 ± 0.17 | 0.02 |
| $T_E$ | 1.32 ± 0.20 | 1.00 ± 0.23 | 0.04 |
| $T_I/T_{tot}$ | 0.50 ± 0.02 | 0.52 ± 0.02 | NS |
| $T_{tot}$ | 2.60 ± 0.30 | 2.02 ± 0.30 | 0.03 |

*Values are means ± SE measured in seconds. Repeated measures ANOVA indicated significant reductions in both $T_I$ and $T_E$ without a change in the duty cycle ratio Ti/Ttot.

The Effects of serotonin Antagonists on the Dynamic Anatomy of the Upper Airway

The cross-sectional areas of the upper airway were compared at three levels: nasopharynx, high retropalatate, and larynx before and after administration of ritanserin at a dose of 0.5 mg/kg to two dogs. In other dogs, data were insufficient either because of movement between the baseline and ritanserin imaging or because of an insufficient number of images per respiratory phase for any an atomic level.

Figure 5B:
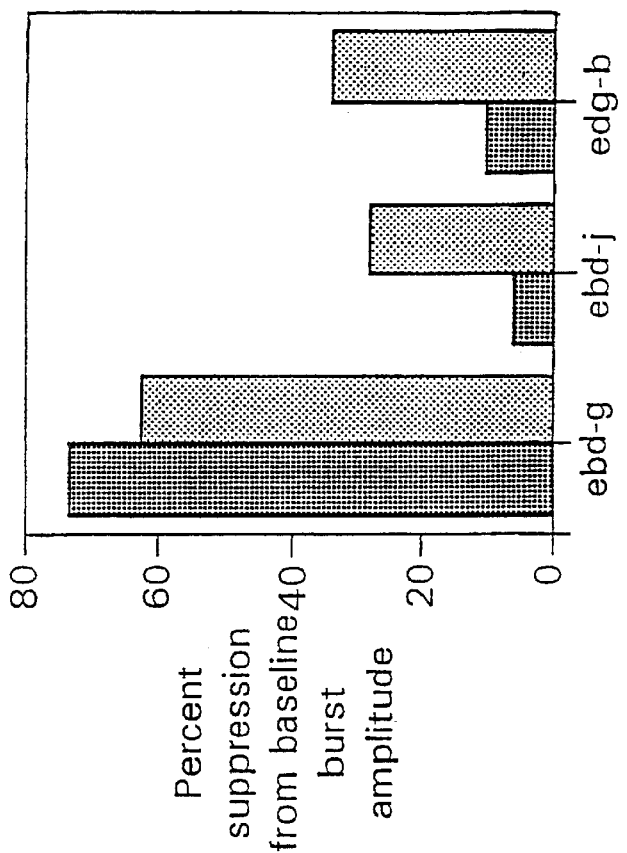
FIGS. 5A and 5B, is a pair of histograms depicting relative suppression of upper airway and diaphragm motor activity induced by systemically administered serotonin antagonists in individual English bulldogs.
Figure 5A:
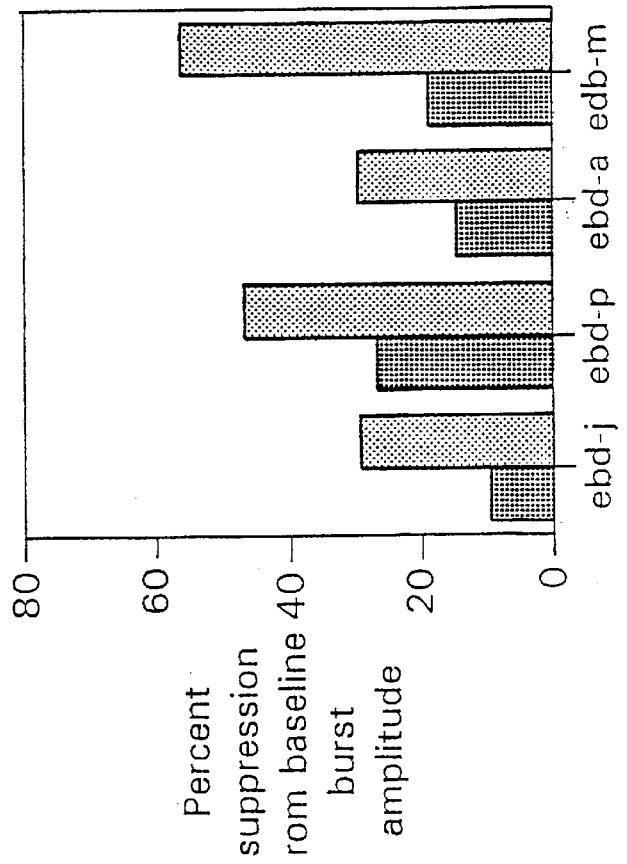
Figure 6:
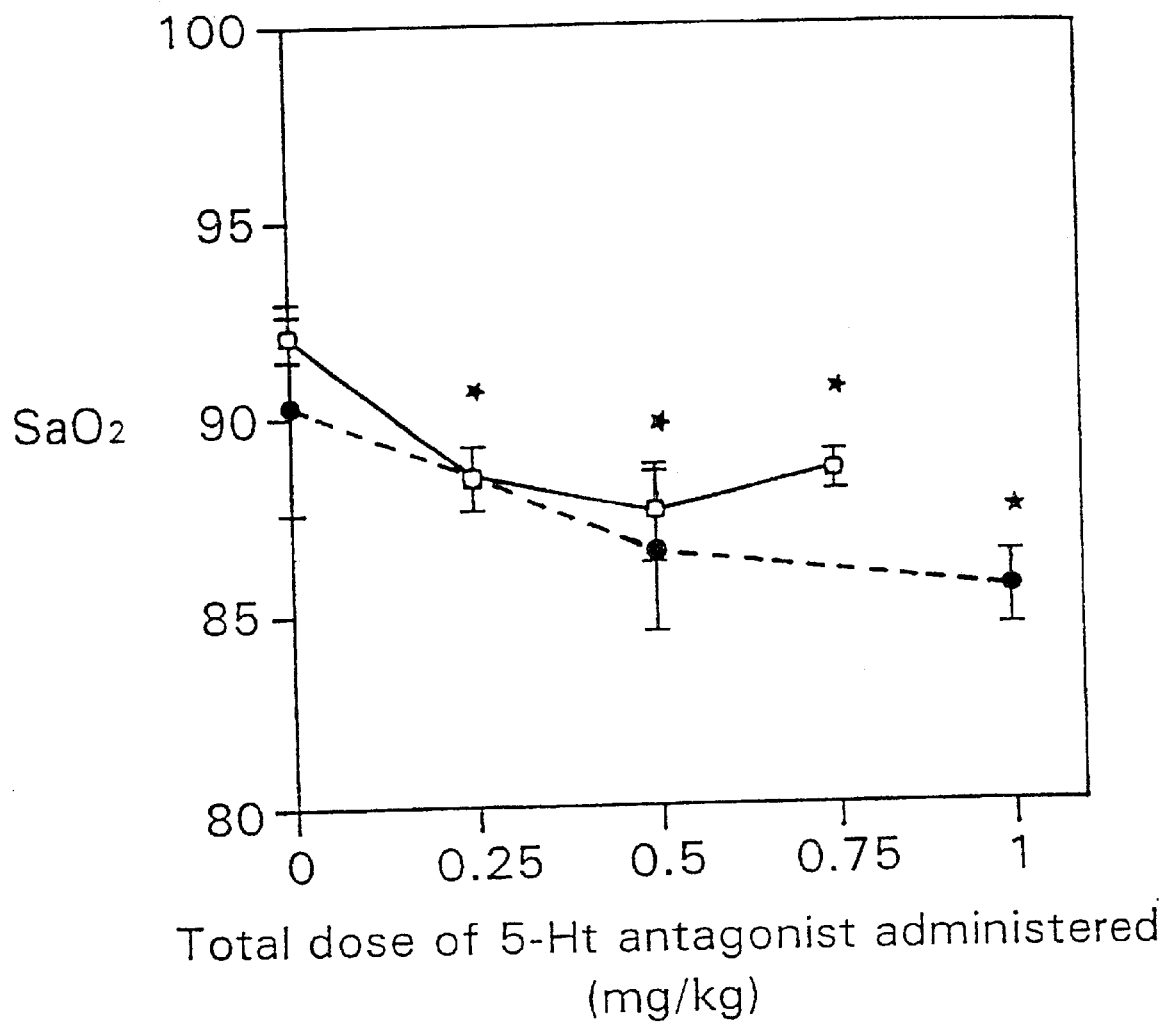
FIG. 6 is a graph indicating the effects of serotonin (5-HT) antagonists waking oxyhemoglobin saturation ($SaO_2$). Mean $SaO_2$ data are presented for ritanserin (solid line, open circles) and for methysergide (dotted line, closed circles). Error bars represent standard error of the mean values. Asterisks highlight significant reductions ($p<0.05$) from baseline values.
Figure 7A:
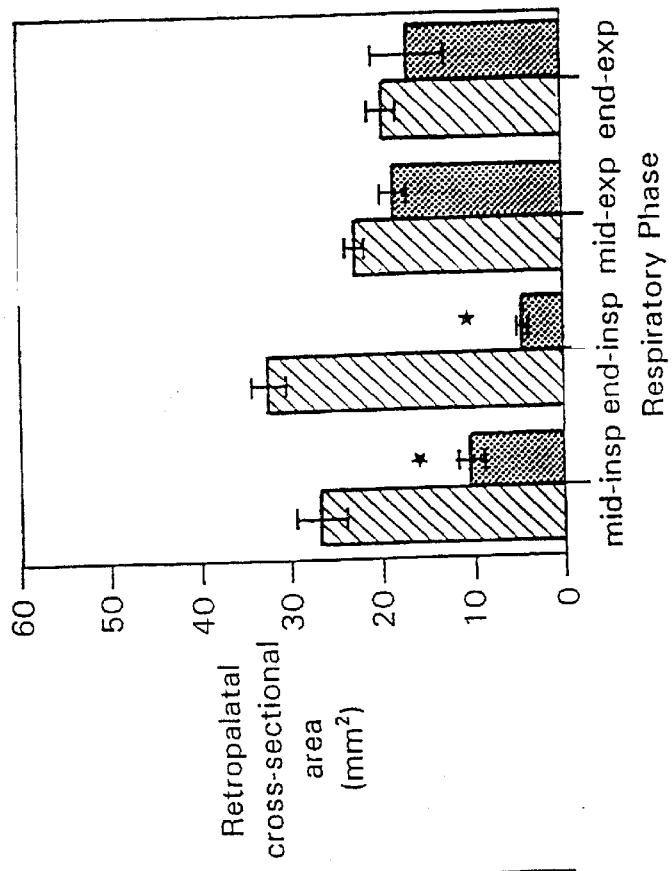
FIGS. 7A, 7B, 7C, and 7D, is a quartet of graphs and histograms which indicate the effects of ritanserin on cross-sectional areas (CSAs) of the retropalatal region of the upper airway. Individual data are presented for two bulldogs BBD-J (FIGS. 7A and 7C) and EBD-M (FIGS. 7B and 7D).
Figure 7B:
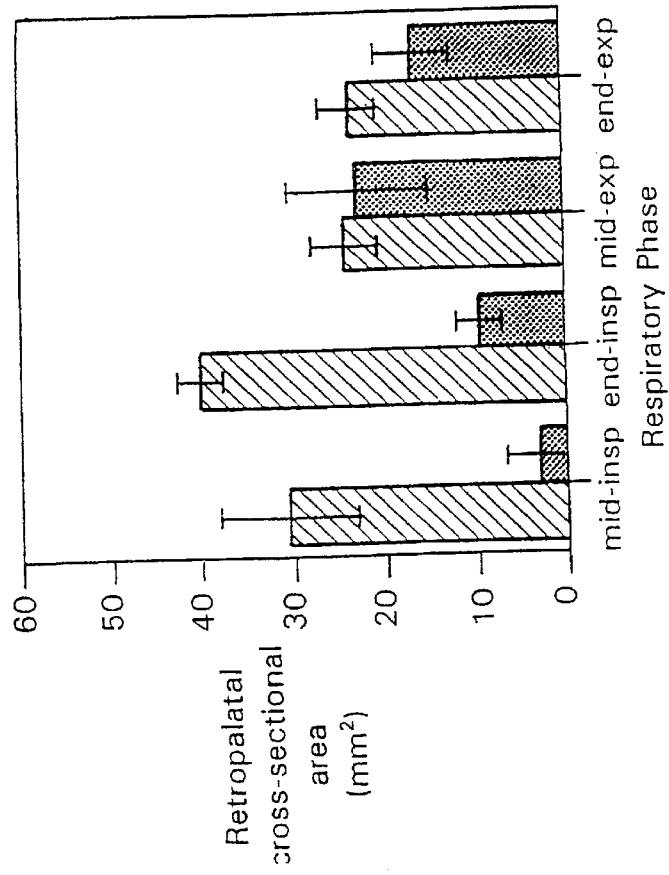
Figure 7D:
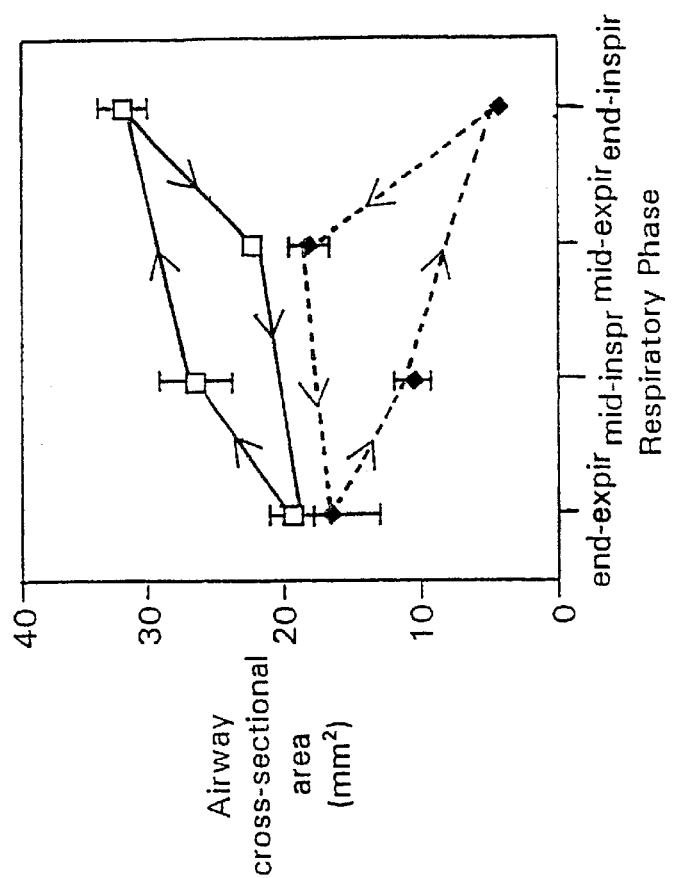
Figure 7C:
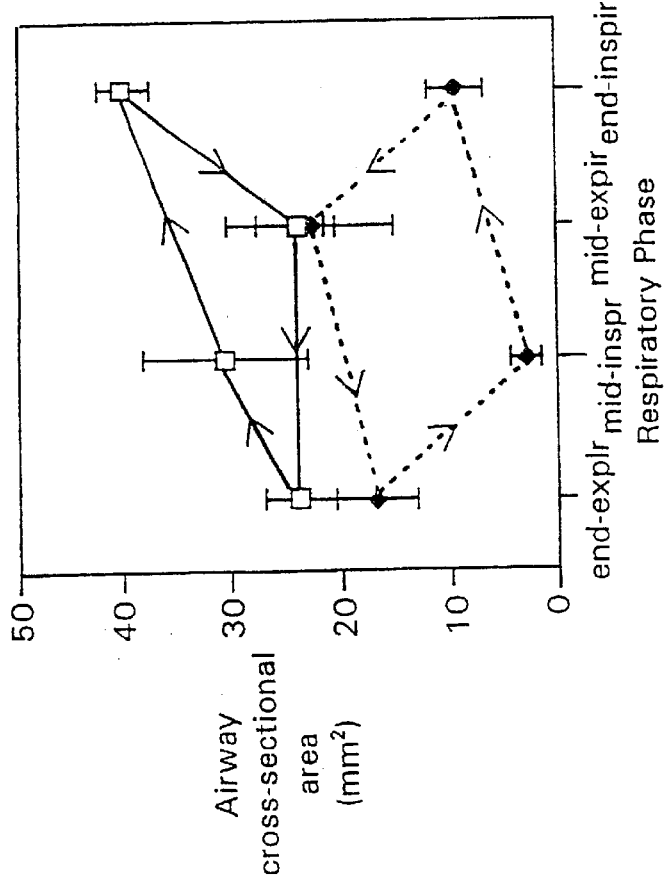

In the two dogs, data were obtained for four phases of the respiratory cycle: mid-inspiration, end-inspiration, mid-expiration, and end-expiration. At baseline, the upper airway region at which the cross-sectional area was least at end-expiration was in the high retropalatal region (midhyoid arch level). In the case of the two dogs in which cross-sectional areas were obtained for the three anatomic levels, data for the retropalatal areas are presented in FIGS. 5A through 5D. FIGS. 5A and 5B indicate actual values for the retropalatal airway CSA at four time points of the respiratory cycle before and after administration of ritanserin. FIGS. 5C and 5D depict the data in FIGS. 5A and 5B, respectively, as respiratory cycle loops of airway cross-sectional area.

Following administration of ritanserin, there was a significant reduction in airway CSA for both stages of inspiration in each dog (individual ANOVAs, p<0.01). However, during expiration, there was no significant changes in the upper airway parameters. Prior to administration of ritanserin, the upper airway area of each dog increased during inspiration. In contrast, there were marked reductions in airway size during the inspiratory phase of the cycle following administration of ritanserin. Coinciding with the reduced inspiratory cross-sectional area, the GH peak amplitude was suppressed by (51.1±1.8)% (mean values for the two dogs), and the chest wall respiratory movement amplitude was reduced by 59.9%. The mean $SaO_2$ was reduced from (92.8±1.8)% to (86.2±4.7)%.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for alleviating or preventing a disordered breathing episode in a mammal, said composition comprising a serotonin re-uptake inhibitor, a TRH agonist, and an agent selected from the group consisting of a serotonin precursor and a serotonin agonist.

2. The composition of claim 1, wherein said serotonin re-uptake inhibitor is selected from the group consisting of trazadone, fluoxetine, and nefazodone.

3. The composition of claim 1, wherein said serotonin precursor is selected from the group consisting of L-tryptophan and L-5-hydroxytryptophan.

4. The composition of claim 1, wherein said serotonin re-uptake inhibitor comprises trazadone, wherein said serotonin precursor comprises L-tryptophan, and wherein the ratio, by weight, of L-tryptophan to trazadone is between about 13.3 to 1 and about 13.5 to 1.

5. The composition of claim 1, wherein said serotonin agonist is selected from the group consisting of serotonin, 5-CT, and DOI.

6. The composition of claim 1, comprising both said serotonin precursor and said serotonin agonist.

7. The composition of claim 1, wherein said TRH agonist is selected from the group consisting of TRH, montirelin, and CG-3703.

8. A kit for alleviating or preventing a disordered breathing episode in a mammal, said kit comprising a serotonin re-uptake inhibitor, a TRH agonist, and an agent selected from the group consisting of a serotonin precursor and a serotonin agonist.

9. The kit of claim 8, wherein said agent is selected from the group consisting of L-tryptophan, L-5-hydroxytryptophan, serotonin, 5-CT, and DOI and is in a unit dosage form.

10. The kit of claim 9, wherein said serotonin re-uptake inhibitor is selected from the group consisting of trazadone, fluoxetine, and nefazodone and is in a unit dosage form.

11. The kit of claim 10, wherein the unit dosage form of said agent is an oral unit dosage form and wherein the unit dosage form of said serotonin re-uptake inhibitor is an injectable solution.

12. The kit of claim 8, further comprising an instructional material describing administration of said serotonin re-uptake inhibitor and said agent for the purpose of alleviating or preventing a disordered breathing episode in a mammal.

* * * * *